US012593984B2

(12) United States Patent
Fujii et al.

(10) Patent No.: US 12,593,984 B2
(45) Date of Patent: Apr. 7, 2026

(54) SYSTEM, INFORMATION STORAGE MEDIUM, AND INFORMATION PROCESSING METHOD

(71) Applicant: OLYMPUS CORPORATION, Tokyo (JP)

(72) Inventors: Masahiro Fujii, Tokyo (JP); Takeshi Arai, Musashino (JP)

(73) Assignee: OLYMPUS CORPORATION, Tokyo (JP)

( * ) Notice: Subject to any disclaimer, the term of this patent is extended or adjusted under 35 U.S.C. 154(b) by 153 days.

(21) Appl. No.: 18/237,732

(22) Filed: Aug. 24, 2023

(65) Prior Publication Data

US 2023/0410298 A1     Dec. 21, 2023

Related U.S. Application Data

(63) Continuation of application No. PCT/JP2022/009692, filed on Mar. 7, 2022.

(Continued)

(51) Int. Cl.
*A61B 5/00*     (2006.01)
*A61B 17/00*     (2006.01)
(Continued)

(52) U.S. Cl.
CPC ............ *A61B 5/0093* (2013.01); *A61B 18/04* (2013.01); *A61B 18/1445* (2013.01);
(Continued)

(58) Field of Classification Search
None
See application file for complete search history.

(56) References Cited

U.S. PATENT DOCUMENTS 8,398,541 B2     3/2013   DiMaio et al.
10,307,209 B1     6/2019   Yu
(Continued)

FOREIGN PATENT DOCUMENTS

EP     3505124 A1     7/2019
EP     3767535 A1     1/2021
(Continued)

OTHER PUBLICATIONS

International Search Report dated May 17, 2022 received in PCT/JP2022/009692.

(Continued)

*Primary Examiner* — Helen Zong
(74) *Attorney, Agent, or Firm* — Scully, Scott, Murphy & Presser, P.C.

(57)     ABSTRACT

The system includes a memory that stores a trained model, and a processor. The processor acquires a pre-treatment image in which at least one energy device and at least one biological tissue are imaged, and a state before application of energy is imaged. The processor estimates an estimated heat diffusion region from the pre-treatment image and information regarding an energy supply amount by processing based on a trained model stored in the memory. The processor superimposes the estimated heat diffusion region on a captured image of the camera and displays the captured image with the superimposed estimated heat diffusion region.

12 Claims, 24 Drawing Sheets

Related U.S. Application Data

(60) Provisional application No. 63/222,252, filed on Jul. 15, 2021, provisional application No. 63/221,128, filed on Jul. 13, 2021.

(51) Int. Cl.

| | |
|---|---|
| *A61B 18/00* | (2006.01) |
| *A61B 18/04* | (2006.01) |
| *A61B 18/14* | (2006.01) |
| *G06T 7/00* | (2017.01) |
| *G06T 7/11* | (2017.01) |
| *G06V 10/25* | (2022.01) |
| *G06V 10/70* | (2022.01) |
| *G16H 30/40* | (2018.01) |
| *G16H 50/20* | (2018.01) |

(52) U.S. Cl.

CPC .............. *G06T 7/0012* (2013.01); *G06T 7/11* (2017.01); *G06V 10/25* (2022.01); *G16H 30/40* (2018.01); *G16H 50/20* (2018.01); *A61B 2017/0042* (2013.01); *A61B 2018/00577* (2013.01); *A61B 2018/00702* (2013.01); *A61B 2018/00791* (2013.01); *A61B 2018/00898* (2013.01); *G06T 2207/10068* (2013.01); *G06T 2207/20081* (2013.01); *G06T 2207/30024* (2013.01); *G06V 10/70* (2022.01)

(56) References Cited

U.S. PATENT DOCUMENTS

| | | | |
|---|---|---|---|
| 10,786,298 | B2 | 9/2020 | Johnson |
| 2008/0082145 | A1 | 4/2008 | Skwarek et al. |
| 2013/0245375 | A1 | 9/2013 | DiMaio et al. |
| 2014/0296842 | A1 | 10/2014 | Mansi et al. |
| 2015/0272653 | A1 | 10/2015 | Brunke et al. |
| 2016/0287338 | A1 | 10/2016 | Grady et al. |
| 2016/0314601 | A1 | 10/2016 | Sankaran et al. |
| 2017/0079678 | A1 | 3/2017 | Ishikawa |
| 2017/0252095 | A1 | 9/2017 | Johnson |
| 2018/0160910 | A1 | 6/2018 | Takahashi et al. |
| 2018/0168734 | A1 | 6/2018 | Strobl |
| 2018/0199987 | A1 | 7/2018 | Sugiyama |
| 2019/0201074 | A1 | 7/2019 | Yates et al. |
| 2019/0201084 | A1 | 7/2019 | Shelton, IV et al. |
| 2019/0206565 | A1 | 7/2019 | Shelton, IV |
| 2019/0262076 | A1 | 8/2019 | Brown |
| 2019/0298398 | A1 | 10/2019 | Wellman et al. |
| 2019/0371474 | A1 | 12/2019 | Borsic |
| 2020/0078081 | A1 | 3/2020 | Jayme et al. |
| 2020/0188046 | A1 | 6/2020 | Overmyer et al. |
| 2020/0197072 | A1 | 6/2020 | Watson |
| 2020/0265309 | A1 | 8/2020 | Wham et al. |
| 2020/0330144 | A1* | 10/2020 | Moriwaki .............. A61B 18/10 |
| 2021/0015554 | A1 | 1/2021 | Chow et al. |
| 2021/0038295 | A1 | 2/2021 | Katsuragi et al. |
| 2021/0038314 | A1* | 2/2021 | Wibowo ................ A61B 18/04 |
| 2021/0085387 | A1 | 3/2021 | Amit et al. |
| 2021/0161588 | A1* | 6/2021 | Fujisawa ................ A61B 90/37 |
| 2021/0196425 | A1 | 7/2021 | Shelton, IV et al. |
| 2021/0267544 | A1 | 9/2021 | Saikou |
| 2021/0401397 | A1 | 12/2021 | Kruecker et al. |
| 2022/0104884 | A1 | 4/2022 | Leiderman et al. |
| 2022/0151721 | A1 | 5/2022 | Haraguchi et al. |
| 2022/0246307 | A1* | 8/2022 | Nakamura ............. G16H 30/40 |
| 2023/0240512 | A1 | 8/2023 | Arai et al. |
| 2023/0380695 | A1 | 11/2023 | Arai et al. |
| 2023/0404652 | A1 | 12/2023 | Uchida et al. |
| 2023/0419486 | A1 | 12/2023 | Nishikawa et al. |

FOREIGN PATENT DOCUMENTS

| | | | |
|---|---|---|---|
| JP | H11-197159 | A | 7/1999 |
| JP | 2018-511403 | A | 4/2018 |
| JP | 2019-170809 | A | 10/2019 |
| JP | 2020-146374 | A | 9/2020 |
| JP | 2021-013722 | A | 2/2021 |
| JP | 2021-029258 | A | 3/2021 |
| JP | 2021-029979 | A | 3/2021 |
| JP | 2021-049341 | A | 4/2021 |
| JP | 2021-083969 | A | 6/2021 |
| JP | 2021-083970 | A | 6/2021 |
| JP | 2021-514724 | A | 6/2021 |
| JP | 2021/188883 | A | 12/2021 |
| WO | 2016/161293 | A1 | 10/2016 |
| WO | 2017/090165 | A1 | 6/2017 |
| WO | 2019134009 | A1 | 7/2019 |
| WO | 2019/162809 | A1 | 8/2019 |
| WO | 2020/031069 | A1 | 2/2020 |
| WO | 2020/051444 | A1 | 3/2020 |
| WO | 2020/095389 | A1 | 5/2020 |
| WO | 2020/104308 | A1 | 5/2020 |
| WO | 2021/039298 | A1 | 3/2021 |
| WO | 2023/286334 | A1 | 1/2023 |

OTHER PUBLICATIONS

K. Naruki, et al., "Proposal for Endoscope Robot with Surgical Scene Recognition using Image Processing", No. 16-2 Proceedings of the 2016 JSME Conference on Robotics and Mechatronics, Yokohama, Japan, Jun. 8-11, 2016, 1A2-02a1(1)-(4), DOI:https://doi.org/10.1299/jsmermd.2016.1A2-02a1.

US Office Action dated Sep. 17, 2025 received in U.S. Appl. No. 18/368,100.

US Office Action dated Sep. 25, 2025 received in U.S. Appl. No. 18/237,599.

US Final Office dated Jan. 8, 2026 received in U.S. Appl. No. 18/368,100.

US Office Action dated Feb. 17, 2026 received in U.S. Appl. No. 18/118,342.

* cited by examiner

FIG.3

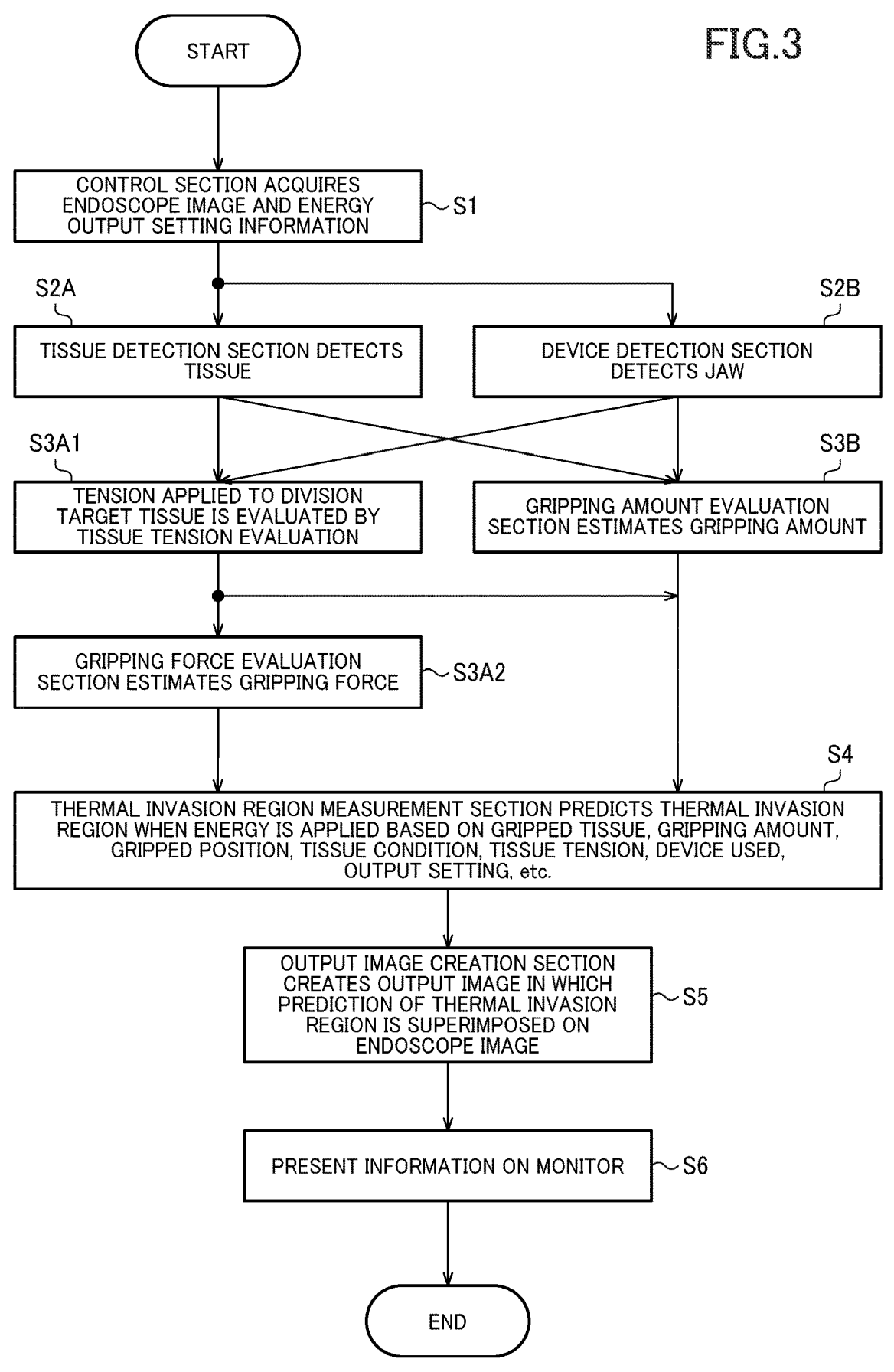

START

CONTROL SECTION ACQUIRES ENDOSCOPE IMAGE AND ENERGY OUTPUT SETTING INFORMATION  ~S1

S2A

TISSUE DETECTION SECTION DETECTS TISSUE

S2B

DEVICE DETECTION SECTION DETECTS JAW

S3A1

TENSION APPLIED TO DIVISION TARGET TISSUE IS EVALUATED BY TISSUE TENSION EVALUATION

S3B

GRIPPING AMOUNT EVALUATION SECTION ESTIMATES GRIPPING AMOUNT

GRIPPING FORCE EVALUATION SECTION ESTIMATES GRIPPING FORCE  ~S3A2

S4

THERMAL INVASION REGION MEASUREMENT SECTION PREDICTS THERMAL INVASION REGION WHEN ENERGY IS APPLIED BASED ON GRIPPED TISSUE, GRIPPING AMOUNT, GRIPPED POSITION, TISSUE CONDITION, TISSUE TENSION, DEVICE USED, OUTPUT SETTING, etc.

OUTPUT IMAGE CREATION SECTION CREATES OUTPUT IMAGE IN WHICH PREDICTION OF THERMAL INVASION REGION IS SUPERIMPOSED ON ENDOSCOPE IMAGE  ~S5

PRESENT INFORMATION ON MONITOR  ~S6

END

FIG. 7
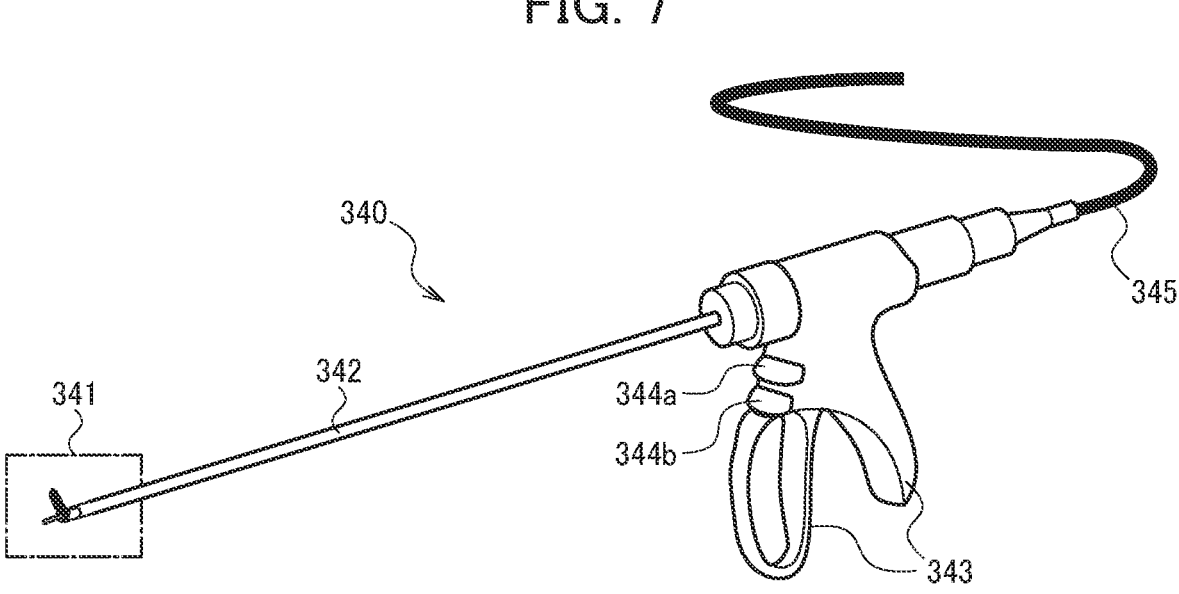
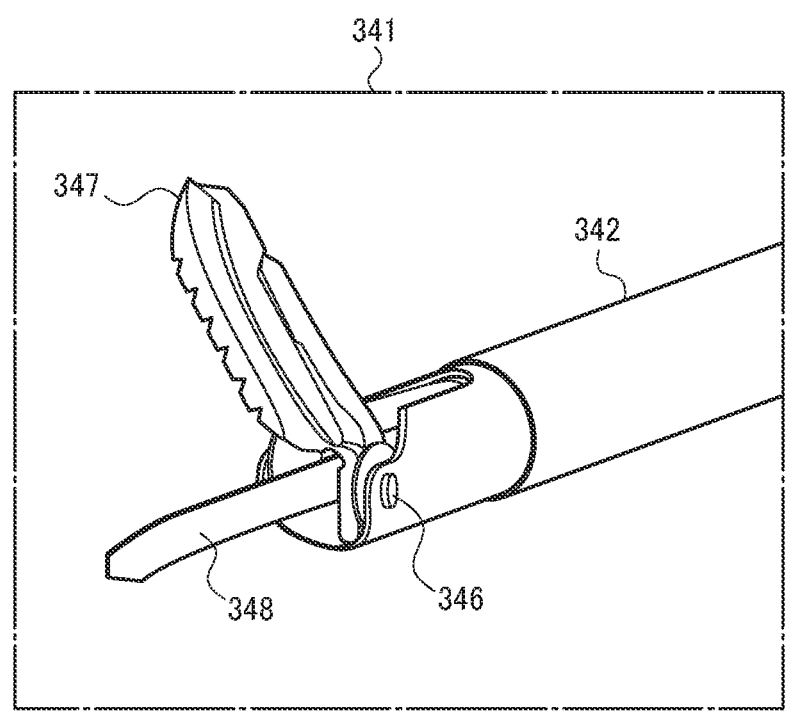

- RANGE OF PRESENCE OF ENERGY DEVICE
- TYPE OF ENERGY DEVICE

TRAINING

- NAME OF TISSUE PRESENT IN SCREEN
- RANGE OF PRESENCE OF EACH TISSUE
- CONDITION OF EACH TISSUE

TRAINING

- NAME AND RANGE OF TREATMENT TARGET TISSUE
- TENSION APPLICATION AMOUNT IN THE REGION

TRAINING

- TENSION APPLICATION AMOUNT
- AMOUNT OF CHANGE OF TISSUE AROUND GRIP SECTION
- GRIPPING FORCE

TRAINING

TRAINING

- TISSUE TYPE
- TISSUE CONDITION
- GRIPPING AMOUNT
- TISSUE TENSION APPLICATION
  AMOUNT
- GRIPPING FORCE
- OUTPUT SETTING
- DEVICE TYPE
- OUTPUT HISTORY
- HEAT DIFFUSION REGION AFTER
  TREATMENT

| TENSION | GRIPPING FORCE | COLOR |
|---------|----------------|-------|
| INTENSE | INTENSE | RED |
| INTENSE | WEAK | YELLOW |
| WEAK | INTENSE | GREEN |
| WEAK | WEAK | BLUE |

SYSTEM, INFORMATION STORAGE MEDIUM, AND INFORMATION PROCESSING METHOD

CROSS REFERENCE TO RELATED APPLICATIONS

This application is a continuation of International Patent Application No. PCT/JP2022/009692, having an international filing date of Mar. 7, 2022, which designated the United States, the entirety of which is incorporated herein by reference. U.S. Patent Applications Nos. 63/221,128 and 63/222,252 filed on Jul. 13, 2021 and Jul. 15, 2021 are also incorporated herein by reference in its entirety.

BACKGROUND OF THE INVENTION

Japanese Unexamined Patent Application Publication No. JP2021-83969 discloses a surgical method using an energy device. In this surgical method, an already-ablated biological tissue region and a not-yet-ablated biological tissue region are displayed on a display using a computed tomography (CT) image. Then, the next biological tissue region toward which energy is to be output is presented to the doctor.

SUMMARY OF THE INVENTION

In accordance with one of some aspect, there is provided a system comprising:

a memory configured to store a trained model that is trained to output a heat diffusion region from a training device tissue image or a training tissue image, the heat diffusion region being a range of reach of heat from the at least one energy device, the training device tissue image being an image in which at least one energy device that receives energy supply to output energy and at least one biological tissue are imaged, the training tissue image being an image in which the at least one biological tissue is imaged; and a processor, wherein the processor is configured to:

acquire a pre-treatment image, in which the at least one energy device and at least one biological tissue are imaged, in which a state before application of energy from the at least one energy device is imaged, and that is captured by a camera that captures an image of a surgical field;

acquire information regarding an energy supply amount to the at least one energy device;

estimate, based on the pre-treatment image, the information regarding the energy supply amount, and the trained model, an estimated heat diffusion region in the pre-treatment image, the estimated heat diffusion region being an estimated range of reach of energy from the at least one energy device after application of the energy based on the energy supply amount; and perform a process of superimposing the estimated heat diffusion region on a captured image of the camera and displaying the captured image with the superimposed estimated heat diffusion region on a display.

In accordance with one of some aspect, there is provided a computer-readable non-transitory information storage medium storing a program for causing a computer to execute acquiring a pre-treatment image, in which at least one energy device and at least one biological tissue are imaged, in which a state before application of energy from the at least one energy device is imaged, and that is captured by a camera that captures an image of a surgical field, and acquiring information regarding an energy supply amount to the at least one energy device, estimating an estimated heat diffusion region in the pre-treatment image by processing based on a trained model, the estimated heat diffusion region being an estimated range of reach of energy from the at least one energy device after application of the energy based on the energy supply amount, the trained model being trained to output a heat diffusion region from a training device tissue image or a training tissue image, the heat diffusion region being a range of reach of heat from the at least one energy device, the training device tissue image being an image in which the at least one energy device and the at least one biological tissue are imaged, the training tissue image being an image in which the at least one biological tissue is imaged, and superimposing the estimated heat diffusion region on a captured image of the camera and displaying the captured image with the superimposed estimated heat diffusion region on a display.

In accordance with one of some aspect, there is provided an information processing method, comprising:

acquiring a pre-treatment image, in which at least one energy device and at least one biological tissue are imaged, in which a state before application of energy from the at least one energy device is imaged, and that is captured by a camera that captures an image of a surgical field, and acquiring information regarding an energy supply amount to the at least one energy device, estimating an estimated heat diffusion region in the pre-treatment image by processing based on a trained model, the estimated heat diffusion region being an estimated range of reach of energy from the at least one energy device after application of the energy based on the energy supply amount, the trained model being trained to output a heat diffusion region from a training device tissue image or a training tissue image, the heat diffusion region being a range of reach of heat from the at least one energy device, the training device tissue image being an image in which the at least one energy device and the at least one biological tissue are imaged, the training tissue image being an image in which the at least one biological tissue is imaged, and superimposing the estimated heat diffusion region on a captured image of the camera and displaying the captured image with the superimposed estimated heat diffusion region on a display.

BRIEF DESCRIPTION OF THE DRAWINGS

FIG. 3 is a flowchart for explaining processing performed by a controller and a system.

FIG. 7 is a configuration example of an ultrasonic device.

DETAILED DESCRIPTION

Figure 1:
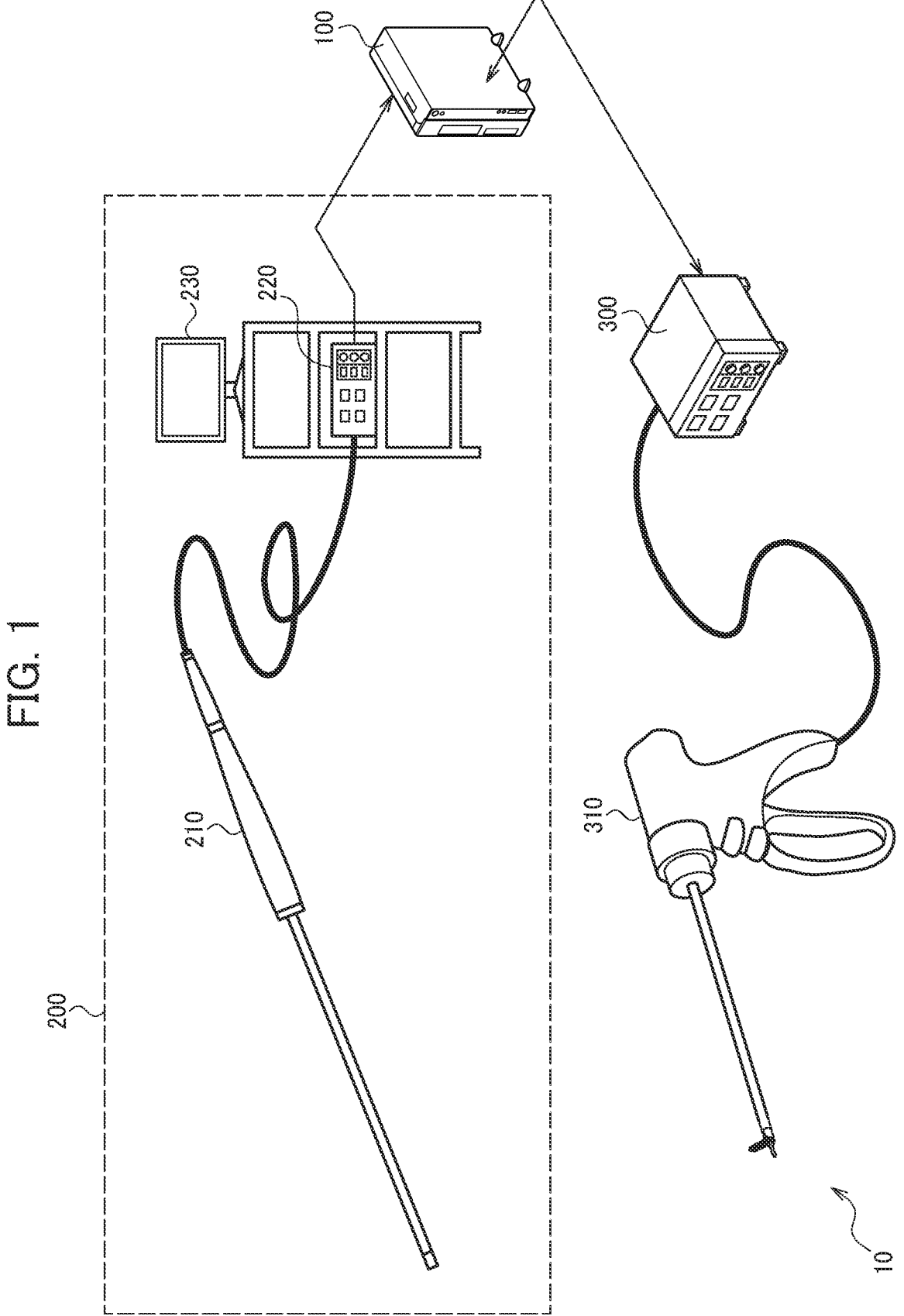
FIG. 1 is a configuration example of a system.

The following disclosure provides many different embodiments, or examples, for implementing different features of the provided subject matter. These are, of course, merely examples and are not intended to be limiting. In addition, the disclosure may repeat reference numerals and/ or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

1. System

FIG. 1 is a configuration example of a system 10 according to the present embodiment. FIG. 1 shows a configuration example of the system for capturing images of a surgical field using an endoscope. The system 10 shown in FIG. 1 includes a controller 100, an endoscope system 200, a generator 300, and an energy device 310. The system 10 is a surgery system for performing surgery using at least one energy device under an endoscope. Although an example in which the system 10 includes a single energy device 310 is shown, the system 10 may include a plurality of energy devices.

The endoscope system 200 is a system that performs imaging by an endoscope, image processing of the endoscope images, and display of the endoscope images in a monitor. The endoscope system 200 includes an endoscope 210, a main body device 220, and a display section 230. Herein, a rigid mirror for surgical operation is described as an example.

The endoscope 210 includes an insertion section to be inserted into a body cavity, an operation section to be connected to the base end of the insertion section, a universal cord connected to the base end of the operation section, and a connector section to be connected to the base end of the universal cord. The insertion section includes a rigid tube, an objective optical system, an imaging sensor, an illumination optical system, a transmission cable, and a light guide. The objective optical system and the imaging sensor for capturing images inside the body cavity and the illumination optical system for illuminating the inside of the body cavity are installed in the distal end section of the rigid tube having an elongated cylindrical shape. The distal end section of the rigid tube may be configured to be bendable. The transmission cable that transmits image signals acquired by the imaging sensor, and the light guide that guides the illumination light to the illumination optical system are provided inside the rigid tube. The operation section is held by the user and accepts operations from the user. The operation section has buttons to which various functions are assigned. When the distal end of the insertion section is bendable, an angle operation lever is provided in the operation section. The connector section includes a video connector that detachably connects the transmission cable to the main body device 220, and a light guide connector that detachably connects the light guide to the main body device 220.

The main body device 220 includes a processing device that controls the endoscope, performs image processing of endoscope images, and displays the endoscope images, and a light source device that generates and controls illumination light. The main body device 220 is also referred to as a video system center. The processing device is constituted of a processor such as a CPU, and performs image processing of the image signals transmitted from the endoscope 210 to generate endoscope images and then outputs the endoscope images to the display section 230 and the controller 100. The illumination light emitted from the light source device is guided by the light guide to the illumination optical system and is emitted from the illumination optical system into the body cavity.

The energy device 310 is a device that outputs energy by high-frequency power, ultrasonic waves, or the like from its distal end section to perform treatments including coagulation, sealing, hemostasis, incision, division, dissection, or the like, with respect to tissues in contact with its distal end section. The energy device 310 is also referred to as an energy treatment tool. The energy device 310 may be a monopolar device in which high-frequency power is energized between an electrode at the distal end of the device and an electrode outside the body, a bipolar device in which high-frequency power is energized between two jaws, an ultrasonic device, which has a probe and a jaw and emits ultrasonic waves from the probe, a combination device in which high-frequency power is energized between the probe and the jaw and also emits ultrasonic waves from the probe, or the like.

The generator 300 supplies energy to the energy device 310, controls the energy supply, and acquires electrical information from the energy device 310. The generator 300 adjusts output of the energy device 310 based on settings made, for example, by a doctor. The generator 300 supplies energy corresponding to the settings by the doctor to the energy device 310, and the energy device 310 receives the energy supply and performs energy output. When the energy device 310 outputs high-frequency energy, the generator 300 provides a high-frequency power, and the energy device 310 outputs the high-frequency power from the electrode or jaw. When the energy device 310 outputs ultrasonic energy, the generator 300 provides electric power, and the probe of the energy device 310 converts the electric power into ultrasonic waves and outputs the ultrasonic waves.

The electrical information refers to electrical information of the tissue that comes in contact with the electrode or jaw of the energy device 310; more specifically, the electrical information is information obtained as a response to the output of the high-frequency power to the tissue by the energy device 310. The electrical information is, for example, impedance information of the tissue to be treated by the energy device 310. However, the electrical information is not limited to impedance information.

The generator 300 performs control of time-based change in the energy output from the energy device 310 according to the output sequence. The generator 300 may vary the energy output according to the time-based change in the impedance information. In this case, the output sequence may specify how the energy output is changed in response to the change in the impedance information. The generator 300 may also automatically turn off the energy output according to the time-based change in the impedance information. For example, the generator 300 may determine that the treatment is completed when the impedance rises to a certain level or higher, and may turn off the energy output.

2. Controller

Figure 2:
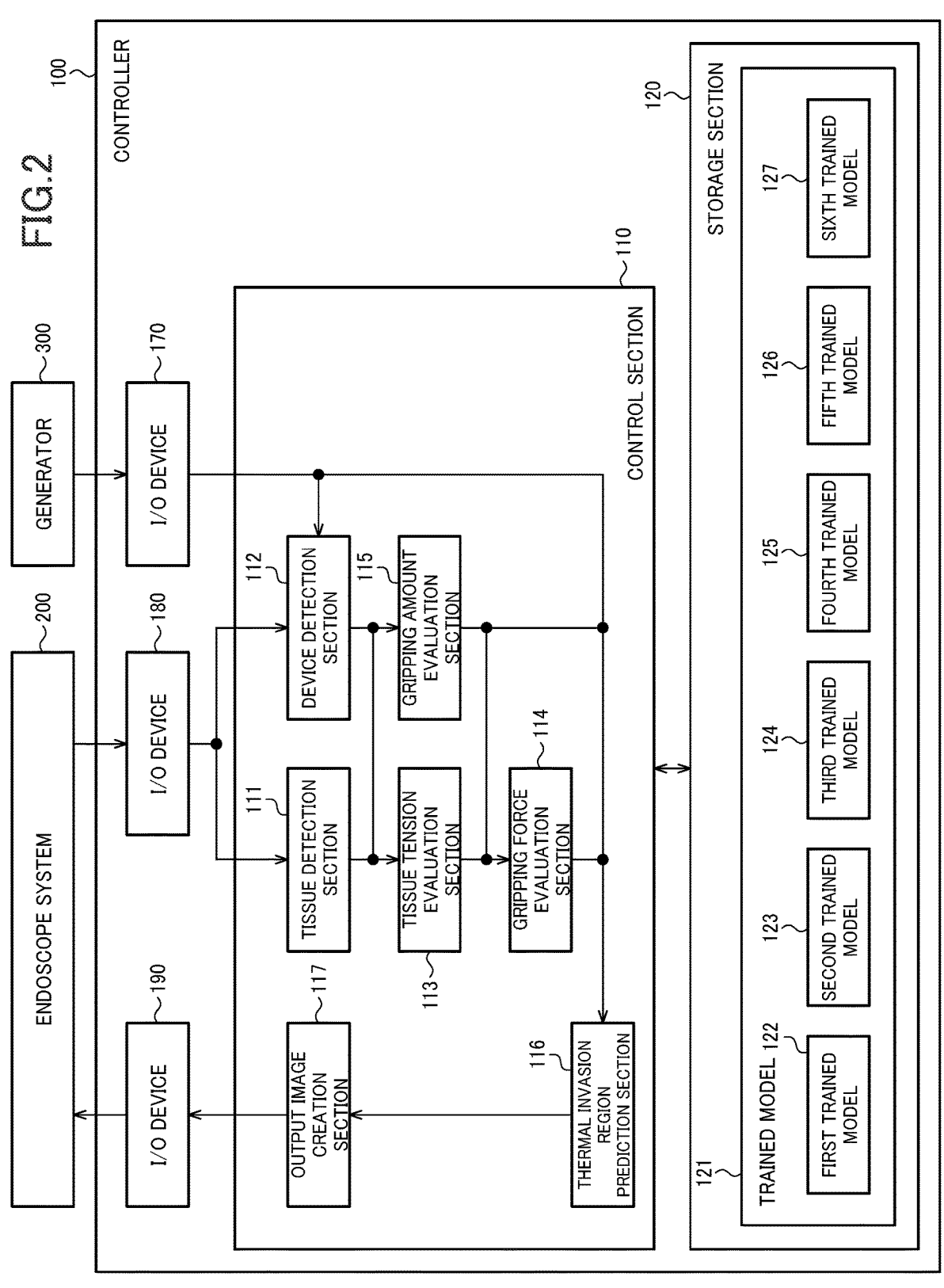
FIG. 2 is a configuration example of a controller.

FIG. 2 is a configuration example of the controller 100. The controller 100 includes a control section 110, a storage section 120, I/O devices 170, 180, and 190. The controller 100 controls the endoscope system 200, the generator 300, and the like, in this system 10. For example, the controller 100 performs various controls through image recognition process using machine learning, and the like. FIGS. 1 and 2 show an example in which the controller 100 is constituted of a device separated from the generator 300. In this case, the controller 100 is constituted of an information processing device, such as a PC, a server device, or the like. Alternatively, the controller 100 may be implemented by, for example, a system that performs the processes with one or a plurality of information processing devices connected via a network, such as a cloud system.

The control section 110 recognizes at least one of the tissue information and the treatment information, which is information regarding the treatment on the biological tissue, from an endoscope image through an image recognition process using a trained model 121, and outputs an energy output adjustment instruction based on the image recognition information. The energy output adjustment instruction may be, for example, an instruction based on a surgeon's operation. The control section 110 includes one or a plurality of processors serving as hardware. The processor is a general-purpose processor such as a CPU (Central Processing Unit), GPU (Graphical Processing Unit), DSP (Digital Signal Processor), or the like. Alternatively, the processor may be a dedicated processor such as an ASIC (Application Specific Integrated Circuit), an FPGA (Field Programmable Gate Array), or the like.

The storage section 120 stores the trained model 121 used for the image recognition process. For example, when the image recognition process is performed by a general-purpose processor, the storage section 120 stores, as the trained model 121, a program that describes an inference algorithm and parameters used for the inference algorithm. When the image recognition process is performed by a dedicated processor with a hardware inference algorithm, the storage section 120 stores the parameters used for the inference algorithm as the trained model 121. The trained model 121 includes a first trained model 122, a second trained model 123, a third trained model 124, a fourth trained model 125, a fifth trained model 126, and a sixth trained model 127. Each trained model is used in each phase of the heat diffusion region estimation process performed by the present system, as explained in FIG. 12 described later. The storage section 120 is a storage device, such as a semiconductor memory, a hard disk drive, an optical disc drive, or the like. The semiconductor memory is, for example, a RAM, a ROM, a nonvolatile memory or the like.

For example, a neural network may be used as the inference algorithm of the image recognition process. Weight coefficients and a bias of the inter-node connections in the neural network correspond to the parameters. The neural network includes an input layer to which image data is entered, an intermediate layer for performing a calculation process with respect to the data input via the input layer, and an output layer for outputting recognition results based on the calculation result output from the intermediate layer. For example, a CNN (Convolutional Neural Network) may be used as the neural network to be used for the image recognition process.

The control section 110 includes a tissue detection section 111, a device detection section 112, a tissue tension evaluation section 113, a gripping force evaluation section 114, a gripping amount evaluation section 115, a thermal invasion region prediction section 116, and an output image creation section 117. The storage section 120 stores a program describing the respective functions of the tissue detection section 111, the device detection section 112, the tissue tension evaluation section 113, the gripping force evaluation section 114, the gripping amount evaluation section 115, the thermal invasion region prediction section 116, and the output image creation section 117. One or a plurality of processors of the control section 110 read out the program from the storage section 120 and execute the program, thereby realizing the respective functions of the device detection section 112, the tissue tension evaluation section 113, the gripping force evaluation section 114, the gripping amount evaluation section 115, the thermal invasion region prediction section 116, and the output image creation section 117 of the control section 110. The program describing the functions of each of these sections may be stored in a non-transitory information storage medium, which is a computer-readable medium. The information storage medium can be implemented by, for example, an optical disc, a memory card, an HDD, a semiconductor memory, or the like. The semiconductor memory is, for example, a ROM or a nonvolatile memory.

The I/O device 180 receives image data of endoscope image from the main body device 220 of the endoscope system 200. Further, the I/O device 190 sends a signal of the output result of the control section 110 to the display section 230. Each of the I/O devices 180 and 190 is a connector to which an image transmission cable is connected, or an interface circuit connected to the connector to perform communication with the main body device 220.

The I/O device 170 transmits a signal regarding energy output adjustment instruction or the like to the generator 300. The energy output adjustment instruction is, for example, an instruction based on the image recognition information or a surgeon's operation. Further, the I/O device 170 receives a signal related to setting information or the like of the generator 300. The I/O device 170 is a connector to which a signal transmission cable is connected, or an interface circuit connected to the connector to perform communication with the generator 300.

FIG. 3 is a flowchart for explaining processing performed by the controller 100 and the system 10.

First, in the step S1, the control section 110 acquires an endoscope image and energy output setting information. The endoscope image can be acquired by the control section 110 from the main body device 220 of the endoscope system 200 via the I/O device 180.

Figure 4:
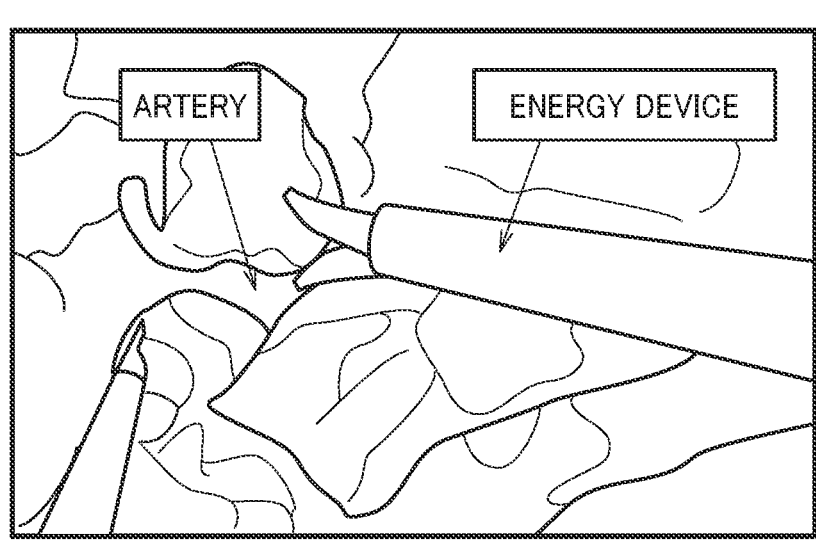
FIG. 4 is an example of a pre-treatment image.

An endoscope image is an image of at least one energy device 310 and at least one biological tissue and shows a state before application of energy from the energy device 310. The endoscope image is an image captured by a camera that captures an image of a surgical field. This image is also referred to as a pre-treatment image. Examples of the camera that captures an image of a surgical field include, but not limited to, the endoscope 210. The image shown in FIG. 4 is an example of a pre-treatment image. The pre-treatment image shown in FIG. 4 has a bipolar device as the energy device 310 and an artery or the like as the biological tissue. The energy output setting information can be acquired by the control section 110 from the generator 300 via the I/O device 170. The energy output setting information is, for example, energy level, energy sequence, or similar information. In this way, in the step S1, the control section 110 acquires information regarding an energy supply amount to be supplied to the energy device 310.

Next, the control section 110 performs the step S2A and the step S2B. In the step S2A, the control section 110 detects a tissue in the tissue detection section 111 based on the pre-treatment image.

In the step S2B, the control section 110 detects jaws 337 and 338 in the device detection section 112 based on the pre-treatment image. The jaws 337 and 338 are explained in FIG. 6, which is described later.

Next, the control section 110 performs the step S3A1, the step S3A2, and the step S3B. In the step S3A1, the control section 110 evaluates the tension applied to a division target tissue in the tissue tension evaluation section 113 based on the detection results in the step S2A and the step A2B. The division target tissue refers to a tissue gripped by a doctor with the energy device 310, which is a tissue toward which energy is about to output. Further, the tension applied to the division target tissue refers to the stress exerted on the tissue gripped by the energy device 310. For example, if a portion of a tissue is gripped and pulled by the energy device 310, the tissue deforms to stretch; in this case, the tension applied on the tissue is high. After the step S3A1 is performed, in the step S3A2, the control section 110 estimates the gripping force by the gripping force evaluation section 114 based on the step S3A1. The gripping force is the strength of the force in gripping the division target tissue with the distal end section, e.g., the jaw, of the energy device 310. Further, the control section 110 performs the step S3B, together with the step S3A1 and the step S3A2.

In the step S3B, the control section 110 estimates the gripping amount based on the detection results in the step S2A and the step S2B in the gripping amount evaluation section 115. Specifically, the gripping amount is a physical length or area of the portion of the biological tissue being gripped by the energy device 310, as explained in FIG. 8 described later.

Next, in the step S4, the control section 110 predicts the thermal invasion region when energy is applied based on information, such as gripped tissue, gripping amount, gripped position, tissue condition, tissue tension, device used, output setting, and the like, in the thermal invasion region prediction section 116. The thermal invasion region refers to a region where heat diffusion occurs when energy is supplied from the energy device 310, and some changes may be caused in the biological tissue by the heat. Such change may specifically be thermal damage such as dena-turation of proteins, inactivation of intracellular enzymes, and the like, in biological tissues. In the following, the thermal invasion region will be referred to as a heat diffusion region, as appropriate. The gripped position is the position of the portion being gripped by the energy device 310 in the biological tissue, which is a treatment target. The gripped position can be predicted based on the results in the step S2A and the step S2B. The tissue condition is the state of tissue that can affect the heat diffusion by the energy device 310. Examples of the tissue condition include the amount of surrounding tissue of the tissue gripped by the jaw, the amount of immersion of the tissue gripped by the jaw or the amount of immersion of surrounding tissue thereof, the amount of fat of the tissue gripped by the jaw, and the like. The amount of immersion is an amount of liquid covering the tissue, e.g., an amount of immersion in body fluids such as blood or lymphatic fluid. The tissue condition can be predicted, for example, based on the results in the step S2A, etc. described above. The output setting is information regarding the energy level, energy sequence, and the like, as described above, which is information regarding the energy supply amount. The control section 110 may acquire this information regarding the energy supply amount, for example, from the generator 300. The tissue tension is as described previously in the description of the tension of the treatment target tissue, and can be acquired as a result of the step S3A1. The gripped tissue can be acquired from the step S2A, the device used can be acquired from the step S2B, and the gripping amount can be acquired from the step S3B.

In this way, in the step S4, the control section 110 estimates the estimated heat diffusion region based on the pre-treatment image, the information regarding the energy supply amount, and the trained model 121. The estimated heat diffusion region is a region in the pre-treatment image, and is an estimated range of reach of energy after application of the energy from the energy device 310 based on the energy supply amount.

Next, in the step S5, the control section 110 creates an output image in which the prediction of the thermal invasion region is superimposed on the endoscope image in the output image creation section 117. Specifically, the predic-tion result of the thermal invasion region is superimposed on the endoscope image by, for example, adding color, to be displayed.

Then, finally, in the step S6, the control section 110 displays the resulting image on the display section 230.

Specifically, the control section 110 outputs the information contained in the image to the endoscope system 200 via the I/O device 190, and the image is displayed on the display section 230 of the endoscope system 200. The display section 230 is, for example, a monitor of a personal computer. In this way, the controller 100 performs a process of causing a display section 230 to superimpose the estimated heat diffusion region on a captured image of the camera to display the estimated heat diffusion region.

3. Energy Device

In the following, a monopolar device 320, a bipolar device 330, an ultrasonic device 340, and a combination device are described as examples of the energy device 310.

Figure 5:
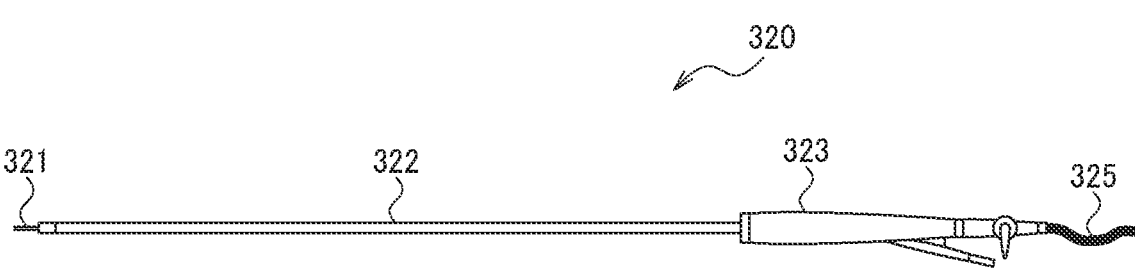
FIG. 5 is a configuration example of a monopolar device.

FIG. 5 is a configuration example of the monopolar device 320. The monopolar device 320 includes an insertion section 322 having an elongated cylindrical shape, an electrode 321 provided at the distal end of the insertion section 322, an operation section 323 connected to the base end of the insertion section 322, and a cable 325 connecting the operation section 323 and a connector (not shown). The connector is detachably connected to the generator 300.

The high-frequency power output by the generator 300 is transmitted by the cable 325 and output from the electrode 321. A counter electrode plate is provided outside the patient's body, and energization occurs between the electrode 321 and the counter electrode plate. This applies high-frequency energy to the tissue in contact with the electrode 321, and Joule heat is generated in the tissue. Electrodes having various shapes are used for the electrode 321 depending on the type of the treatment. The monopolar device 320 is capable of adjusting the degree of coagulation and incision by changing the energization pattern. Generally, the target object to be treated by the monopolar device 320 is the tissue in contact with the electrode 321, and the heat diffused around this tissue in contact with the electrode 321 may affect the surrounding tissue.

Figure 6:
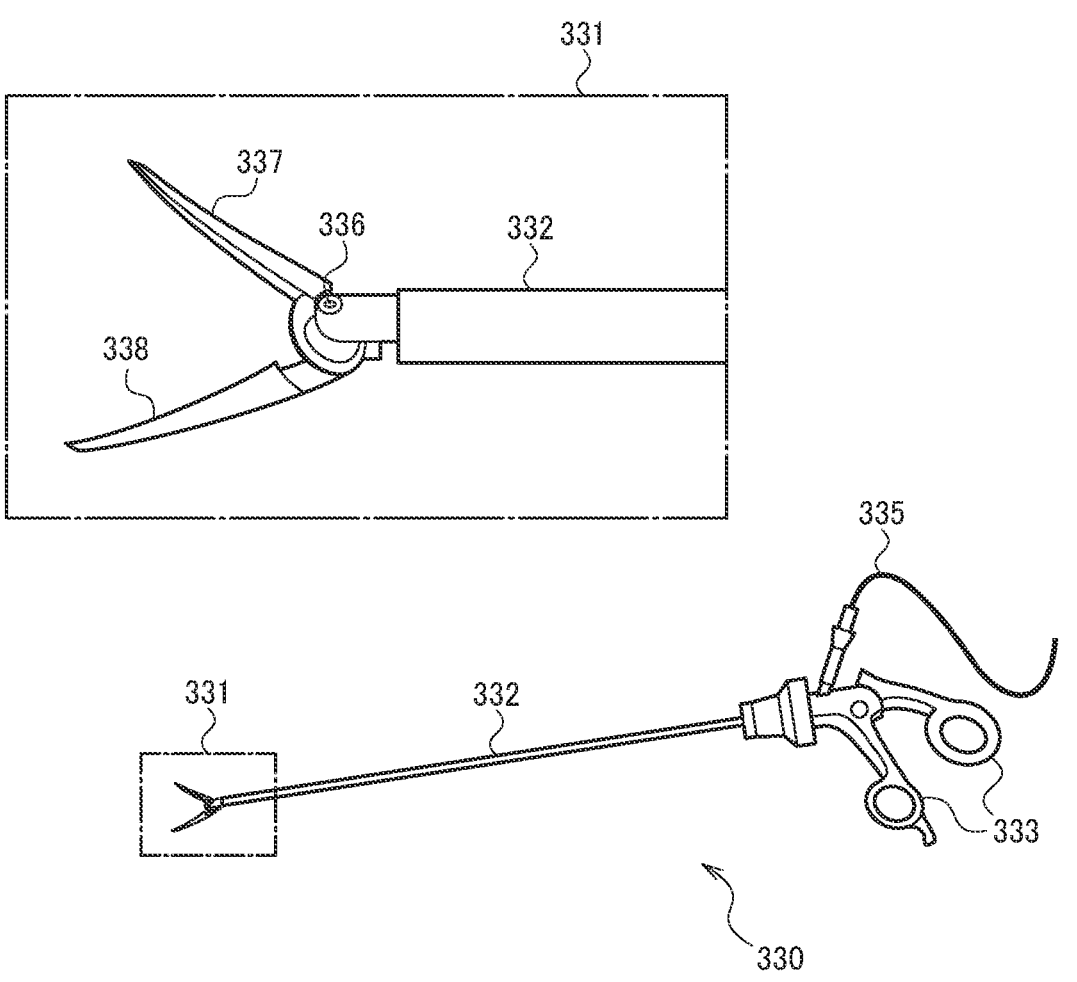
FIG. 6 is a configuration example of a bipolar device.

FIG. 6 is a configuration example of a bipolar device 330. The bipolar device 330 includes an insertion section 332 having an elongated cylindrical shape, two jaws 337 and 338 provided at the distal end section 331 of the insertion section 332, an operation section 333 connected to the base end of the insertion section 332, and a cable 335 connecting the operation section 333 and a connector (not shown). The connector is detachably connected to the generator 300. The jaws 337 and 338 are movable portions for gripping a tissue and also for applying energy to the gripped tissue. The jaws 337 and 338 are structured to be openable/closable around an axis provided at the base end 336. The operation section 333 has a grip section for operating the opening and closing of the jaws 337 and 338. When the doctor tightly holds the grip section, the jaws 337 and 338 are closed to grip the tissue.

The high-frequency power output by the generator 300 is transmitted by the cable 335, and, when the jaws 337 and 338 grip a tissue, energization occurs between the two jaws 337 and 338. As a result, high-frequency energy is applied to the tissue sandwiched between the two jaws 337 and 338, Joule heat is generated in the tissue, and the tissue is coagulated. The generator 300 may measure the impedance information of the tissue gripped by the jaws 337 and 338, detect completion of the treatment based on the impedance information, and may automatically stop the energy output. Further, the generator 300 may also automatically adjust the energy applied to the tissue based on the impedance information. For example, although the device temperature of the bipolar device 330 rises only to about 100 degrees Celsius, there is a possibility that a sneak current is generated around the area gripped by the jaws 337 and 338, and heat diffusion may be generated by the sneak current.

A vessel sealing device is a derivative device of the bipolar device. The vessel sealing device is a bipolar device provided with a cutter on its jaw, and separate the tissue by running the cutter after coagulating the tissue by energization.

FIG. 7 is a configuration example of the ultrasonic device 340. The ultrasonic device 340 includes an insertion section 342 having an elongated cylindrical shape, a jaw 347 and a probe 348 provided at a distal end section 341 of the insertion section 342, an operation section 343 connected to the base end of the insertion section 342, and a cable 345 connecting the operation section 343 and a connector (not shown). The connector is detachably connected to the generator 300. The jaw 347 is movable around an axis provided at the base end 346, and is structured to be openable/closable with respect to the non-movable probe 348. The operation section 343 has a grip section for operating the opening and closing of the jaw 347. When the doctor tightly holds the grip section, the jaw 347 is closed, and the jaw 347 and the probe 348 grip the tissue. The operation section 343 is provided with an operation button 344a to which a first output mode is assigned, and an operation button 344b to which a second output mode is assigned. The output mode is selected according to what treatment is to be performed. When the operation button for each output mode is pressed, ultrasonic energy is output in the output sequence for the corresponding mode.

The power output by the generator 300 is transmitted by the cable 335, and when the operation button 344a or the operation button 344b is pressed, the probe 348 converts the power into ultrasonic waves and outputs the ultrasonic waves. As a result, a frictional heat is generated in the tissue sandwiched between the jaw 347 and the probe 348, and the tissue is coagulated or incised. Generally, although the heat diffusion of the ultrasonic device 340 is smaller than that of the high-frequency device, the device temperature of the ultrasonic device 340 can rise to nearly 200 degrees Celsius. The heat diffusion of the ultrasonic device 340 is characterized by its tendency to occur in the direction of the distal end of the probe 348.

The combination device that uses both high-frequency power and ultrasonic waves has a configuration similar to that of the ultrasonic device shown in FIG. 6, for example. However, the combination device is capable of energizing high-frequency power between the jaw and the probe to generate Joule heat in the tissue gripped by the jaw and the probe, thus coagulating the tissue. Similarly to the ultrasonic device, the combination device is also capable of incising a tissue gripped by the jaw and the probe by outputting ultrasonic waves from the probe. A high-frequency mode is assigned to one of the two operation buttons provided on the operation section, and a seal-and-cut mode is assigned to the other one of the two operation buttons. The high-frequency mode is a mode in which coagulation and other treatments are performed using only high-frequency energy output. The seal-and-cut mode is a mode in which high-frequency energy and ultrasonic energy are used in combination, and the tissue is coagulated and separated by high-frequency energy output. With regard to the heat diffusion of the combination device, for example, heat diffusion similar to either or both of those of the bipolar device and the ultrasonic device may occur.

In the following embodiment, an exemplary case where the bipolar device 330 is mainly used as the energy device 310 is described. However, it should be noted that the present embodiment is applicable to any cases of using various energy devices mentioned above that may cause heat diffusion.

4. First Embodiment

Figure 8:
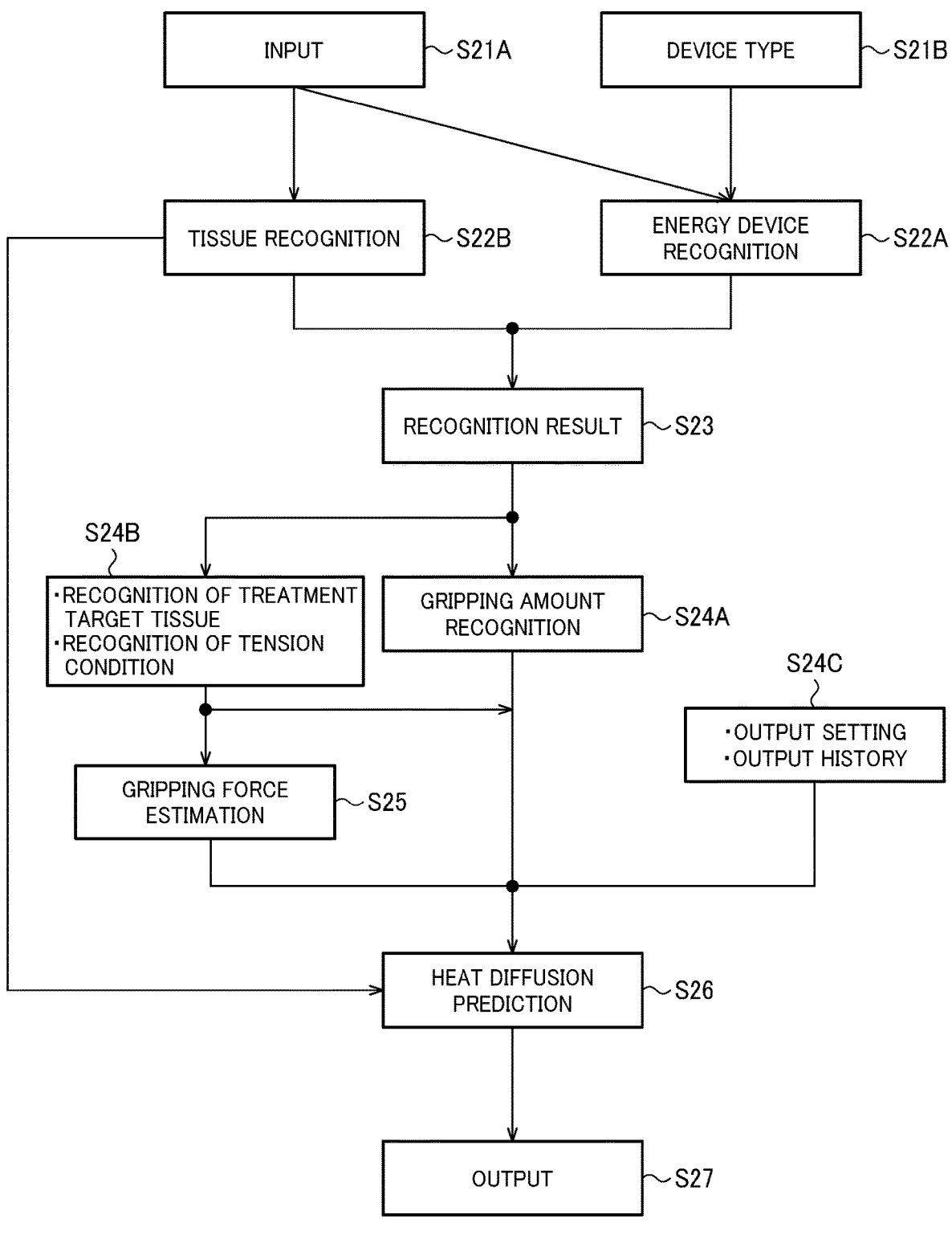
FIG. 8 is an example of processing according to a first embodiment.

FIG. 8 is the first embodiment of an example of processing of the present system. First, the control section 110 performs the processing shown in S21A and S21B. Specifically, in the input shown in S21A, the control section 110 acquires a pre-treatment image. Then, in S21B, the control section 110 acquires the device type. The device type can be acquired from the information detected by the device detection section 112. Then, in S21A, the control section 110 inputs the acquired pre-treatment image as output information to the device detection section 112, which performs the processing in S22A, and the tissue detection section 111, which performs the processing in S22B. Further, in S22B, the control section 110 inputs the information regarding the acquired device type as output information to the device detection section 112, which performs the processing in S22A.

Next, the control section 110 performs the processing shown in S22A and S22B. In S22A, recognition of the energy device 310 is performed. Specifically, the device detection section 112 detects the energy devices 310 from the pre-treatment image by executing an estimation program adjusted by machine learning. The estimation program is a program that executes the trained model 121 that has been trained to estimate the type of the energy device 310 from the subject captured in the pre-treatment image, as explained in FIG. 12, which is described later. In S22A, the device detection section 112 detects the energy device 310 by inputting the pre-treatment image captured during a surgery acquired in S21A to the network having the estimation program. At this time, the information of the device type acquired in S21B or the information regarding the energy supply amount may also be input to the network, together with the pre-treatment image. The targets to be estimated in the processing in S22A also include information such as the range in which the energy device 310 is present, the state of the distal end section of the energy device 310, and the like, in addition to the type of the energy device 310. The state of the distal end section is, for example, the state whether the jaws 337 and 338 are opened/closed. These types of information about the energy device 310 is referred to as device information. The device detection section 112 then labels the portion corresponding to the region of the energy device 310 detected in the pre-treatment image by, for example, adding a color.

Figure 9:
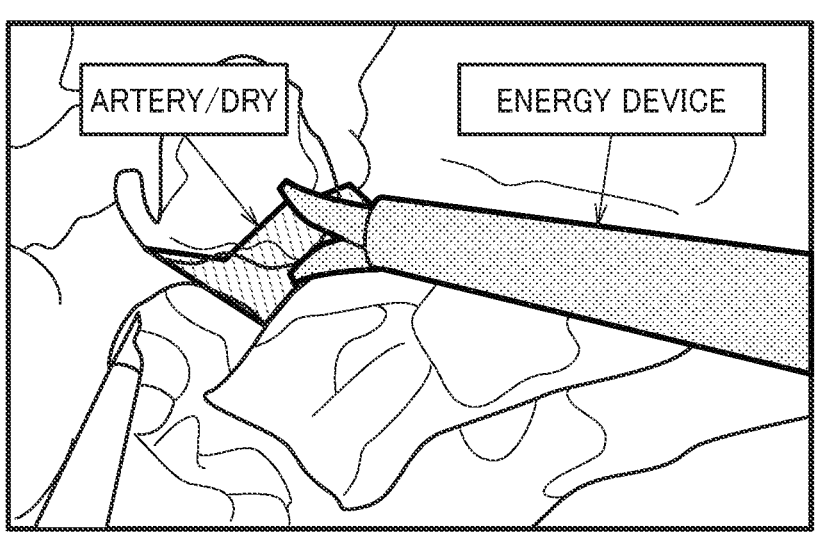
FIG. 9 is a display example of tissue information and device information.

In S22B, the tissue detection section 111 of the control section 110 performs recognition of the tissue of the control section 110. The tissue detection section 111 detects a biological tissue from the pre-treatment image by executing the estimation program. The estimation program is a program that executes the trained model 121 that has been trained to estimate the type of the biological tissue or the like from the subject captured in the pre-treatment image, as explained in FIG. 12, which is described later. In S22B, the tissue detection section 111 detects the tissue information by inputting the pre-treatment image acquired in S21A to the network having the estimation program. The tissue information herein includes the tissue type, the range in which the tissue is present, the tissue condition, and the like, of the biological tissue in the pre-treatment image. The tissue condition includes, for example, wet, dry, the presence or absence of discoloration, or the like. Examples of the biological tissue include large blood vessels, pancreas, duodenum, as well as the parts connecting the tissues, vessels such as arteries or veins, and the like. The biological tissue may also be simply referred to as a tissue. Then, labeling of the biological tissue type detected above is performed. The labeling is performed, for example, by coloring a portion as a region of a biological tissue. The image shown in FIG. 9 is an example of an image in which labels are added to the energy device 310 and the treatment target tissue detected in S24A and S24B. In the image shown in FIG. 9, each of the energy device 310 and the treatment target tissue is labelled by being surrounded by a frame with textual information. In the example of FIG. 9, it is indicated that the treatment target tissue is an artery, and the tissue condition is dry. In this way, the tissue detection section 111 extracts, from the pre-treatment image, tissue information regarding the biological tissue imaged in the pre-treatment image.

Then, the pre-treatment image to which labels are added in S22A and S22B serves as the recognition result in S23. The control section 110 inputs the recognition result to the tissue tension evaluation section 113, which performs the processing in S24A, and the gripping amount evaluation section 115, which performs the processing in S24B. The input of the device type in S22A and the input of the tissue information in S22B may be manual input by the doctor. In the tissue recognition in S22B, the detection of biological tissue may also be performed by 3D matching with CT (Computed Tomography) or MRI (Magnetic Resonance Imaging), instead of endoscope image.

Figure 10:
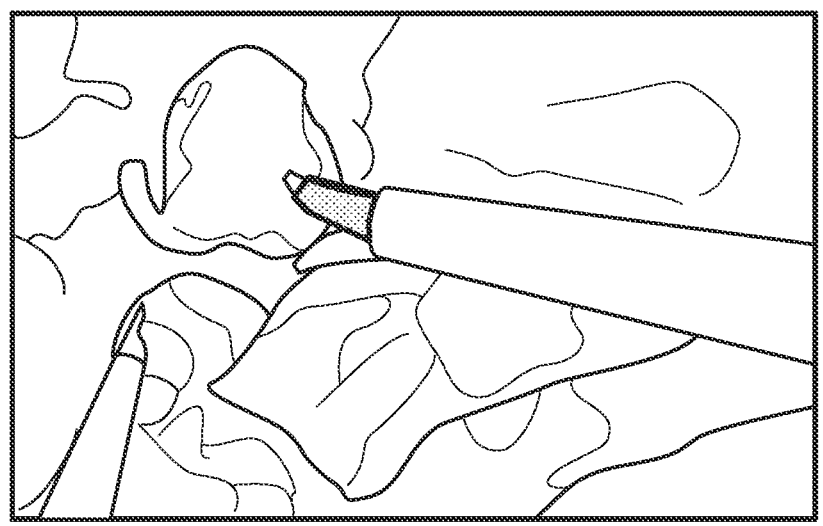
FIG. 10 is an example of an image labeled with an amount of gripped tissue.

Next, the control section 110 performs S24A, S24B and S24C. First, in S24A, the gripping amount evaluation section 115 estimates the amount of gripped tissue, which is the treatment target. Specifically, the gripping amount evaluation section 115 estimates the amount of the gripped tissue, which is the treatment target, based on the recognition result in S23 by executing the estimation program. The estimation program is a program that executes the trained model 121, which has been trained to estimate the amount of gripped tissue, which is the treatment target, based on the information regarding the energy device 310 and the information regarding the biological tissue. In this program, the gripping amount is determined, for example, according to the size of overlap of each segmented subject. In S24A, the gripping amount evaluation section 115 calculates the amount of gripped tissue from the recognized image by inputting the information of the recognition result in S23 to the network having the estimation program. The tissue gripping amount herein refers to a physical length or area of the portion of the biological tissue being gripped by the energy device 310. Then, labeling of the tissue gripping amount detected above is performed. The image shown in FIG. 10 is an example of an image in which a label of the tissue gripping amount estimated in S24A is added by the gripping amount evaluation section 115. As shown in FIG. 10, the label of the tissue gripping amount is added by displaying a frame surrounding the portion gripping the tissue in the distal end section of the energy device 310. The labeling method is not limited to the example shown in FIG. 10. The gripping amount evaluation section 115 then inputs the information including the labelled image to the thermal invasion region prediction section 116, which performs the processing in S26.

In S24B, the tissue tension evaluation section 113 recognizes the tension condition of the treatment target tissue. Specifically, the tissue tension evaluation section 113 estimates the tension condition of the treatment target tissue based on the recognition result in S23 by executing the estimation program. As explained in FIG. 12, which is described later, the estimation program is a program that executes the trained model 121, which has been trained to estimate the tension condition of the treatment target tissue from the information regarding the energy device 310 and the information regarding the biological tissue in S23. If the tension is too weak, the tissue may not be cut easily and the heat may spread, which may affect the result of estimation of the heat diffusion region. The tension is as described in FIG. 3. The tension in the treatment target tissue is also referred to as a tension applied to the biological tissue.

In S24B, the tissue tension evaluation section 113 estimates the tension condition of the treatment target tissue from the recognized image by inputting the information of the recognition result in S23 to the network having the estimation program. To estimate the tension condition, for example, during the training phase, training is performed by learning how it looks when tension is applied on a certain tissue for each of various cases, and then, in the actual surgery, estimation is performed as to how much tension is applied to the tissue currently gripped by calculating backward from the acquired pre-treatment image. Then, the tissue tension evaluation section 113 inputs the information about the estimated tension condition to each of the gripping force evaluation section 114, which performs the processing in S25, and the thermal invasion region prediction section 116, which performs the processing in S26.

In S24C, the control section 110 acquires information about output setting and output history. The output setting is the same as the output setting information described in FIG. 3. The output history is history information about energy levels, output settings, and the like, of the output from the energy device 310. Examples thereof include information such as the amount of residual heat, or the number of times of consecutive cutting before the treatment by the energy device 310. For example, immediately after turning off the output of the energy device 310, there may be residual heat. Therefore, since the initial conditions upon heat diffusion are different, the region where heat diffuses is also different. In this regard, the output history is important in the estimation of the heat diffusion region. These items of information can be acquired, for example, from the generator 300. The control section 110 then inputs the information about the acquired output setting and output history to the thermal invasion region prediction section 116.

Next, the control section 110 estimates the gripping force shown in S25. Specifically, the gripping force evaluation section 114 executes the estimation program to estimate the gripping force in gripping the tissue by the energy device 310. The estimation program is a program that executes the trained model 121, which has been trained to estimate the gripping force in gripping the tissue, based on the information of tissue tension condition estimated in S24B. In S25, the gripping force evaluation section 114 estimates the gripping force by inputting the information of tissue tension condition to the network having the estimation program. The method of estimating the gripping force is, for example, such that, in the training phase, training is performed to learn the relationship between the gripping force applied by the energy device 310 and the amount of change in tissue, e.g., the size, color, reflectance, and the like, before and after the gripping regarding the tissue around the grip section. The gripping force is then estimated from the history of the pre-treatment image acquired during the actual surgery.

The gripping force evaluation section 114 inputs the information including the estimation result to the thermal invasion region prediction section 116, which performs the processing in S26.

Figure 11:
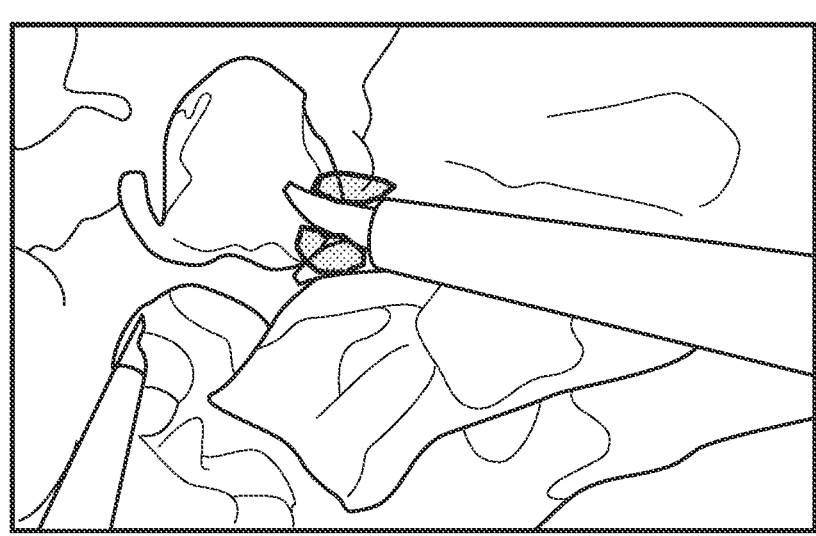
FIG. 11 is an example of an image labeled with an estimated heat diffusion region.

Next, the control section 110 performs prediction of the heat diffusion region as shown in S26. Specifically, the thermal invasion region prediction section 116 of the control section 110 executes the estimation program to estimate the range of heat diffusion when the energy device 310 outputs energy. The estimation program is a program that executes the trained model 121 that has been trained to estimate the range of heat diffusion based on information about the type and tension condition of the treatment target tissue, the amount of gripped tissue and force in gripping the tissue by the energy device 310, and the output setting and output history of the energy device 310. In S26, the thermal invasion region prediction section 116 estimates the heat diffusion region from the recognized image by inputting such information to the network having the estimation program. The heat diffusion region is as described in step S4 in FIG. 3. Then, labeling of the heat diffusion region detected above is performed. In this way, the control section 110 estimates the estimated heat diffusion region in the treatment target tissue to be treated by the energy device 310 based on the pre-treatment image, the information regarding energy supply amount, and the trained model 121. The image shown in FIG. 11 is an example of an image with a label of estimated heat diffusion region estimated in S26. As shown in FIG. 11, the heat diffusion regions are shown by being surrounded by a frame around the jaw in the distal end section of the energy device 310. For example, labeling of heat diffusion region on the screen may be done by coloring the corresponding region. The thermal invasion region prediction section 116 then inputs the information including the labelled image to the output image creation section 117, which performs the processing in S27.

Finally, the control section 110 performs the output shown in S27. Specifically, the output image creation section 117 of the control section 110 creates an image to be displayed on the display section 230 of the endoscope system 200 based on the information including the image created by the thermal invasion region prediction section 116 in S26. For example, the output image is created by superimposing the information, such as the energy device 310 and the tissue recognized in S22A and S22B, or the gripping amount or the like recognized in S24A, on the image labelled with the heat diffusion region in S26. In this way, the output image creation section 117 superimposes the estimated heat diffusion region on the estimated biological tissue region around the energy device 310 to display the estimated heat diffusion region. The display of superimposed estimated heat diffusion region may be performed by superimposing the estimated heat diffusion region on the energy device 310. The output image creation section 117 inputs the output information including the output image thus created to the endoscope system 200 via the I/O device 190. Then, the display section 230 of the endoscope system 200 displays the output image, thereby making it possible to present the heat diffusion region to the doctor.

Figure 12:
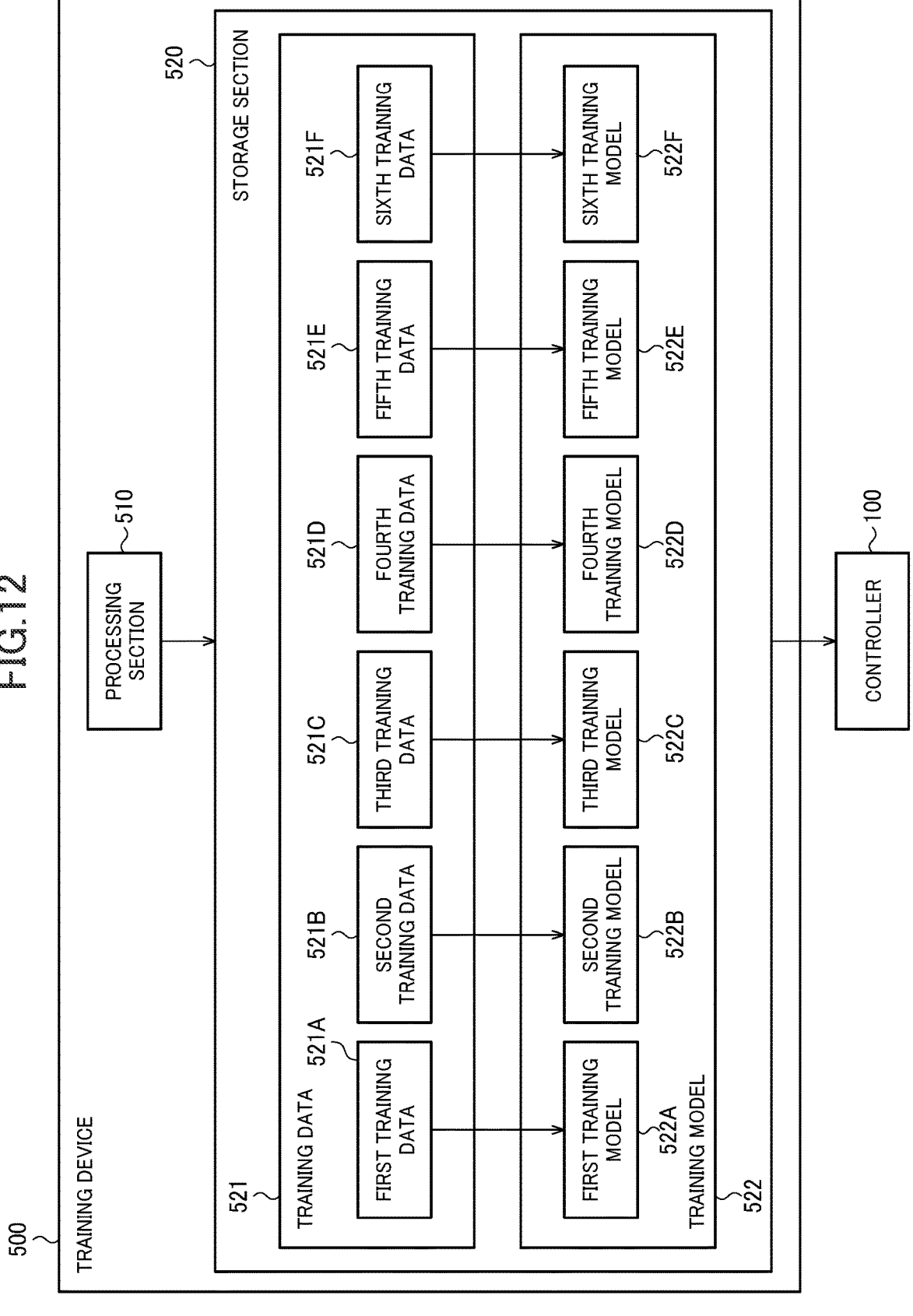
FIG. 12 is a configuration example of a training device.

FIG. 12 is a configuration example of the training device 500, which performs machine learning in the present system. The training device 500 includes a processing section 510 and a storage section 520. The training device 500 is implemented by an information processing device, such as a PC, a server device, or the like. Alternatively, the training device 500 may be implemented by a cloud system that performs the processes with one or a plurality of information processing devices connected via a network.

The processing section 510 is a processor such as a CPU or the like, and the storage section 520 is a storage device such as a semiconductor memory, a hard disc drive, or the like. The storage section 520 stores training data 521 and a training model 522. The training data 521 includes first training data 521A, second training data 521B, third training data 521C, fourth training data 521D, fifth training data 521E and sixth training data 521F. The training model 522 includes a first training model 522A, a second training model 522B, a third training model 522C, a fourth training model 522D, a fifth training model 522E, and a sixth training model 522F. The processing section 510 uses the training data 521 to train the training model 522 to generate a trained model 121.

The training data 521 includes a training device tissue image in which at least one energy device 310 which receives energy supply and performs energy output and at least one biological tissue are imaged, or a training tissue image in which at least one biological tissue is imaged. In each of the training device tissue image and the training tissue image, correct answer data is added. The correct answer data are annotations in the segmentation (region detection) in machine learning, annotations in the detection (location detection), correct answer labels in the classification (classification), or correct answer labels in the regression (regression analysis). In the following description, the training device tissue image and the training tissue image may be collectively referred to as a training image.

The first training data 521A is the training data 521 regarding the energy device 310. The second training data 521B, the third training data 521C, the fourth training data 521D, the fifth training data 521E, and the sixth training data 521F are training data regarding the biological tissue, the amount of gripped biological tissue, the tension condition of the biological tissue, the gripping force in gripping the biological tissue, and the heat diffusion range, respectively. The training model 522 has the same correspondence, i.e., the first training model 522A, the second training model 522B, the third training model 522C, the third training model 522D, the third training model 522E, and the third training model 522F are training model regarding the energy device 310, the biological tissue, the amount of gripped biological tissue, the tension condition of the biological tissue, the gripping force in gripping the biological tissue, and the heat diffusion range, respectively. For example, the processing section 510 inputs a training image, which is the first training data 521A about the energy device 310, to the inference process by the first training model 522A about the energy device 310. Then, feedback is given to the first training model 522A based on the error between the results of the inference process and the first training data 521A. This process is repeated using a large number of first training data 521A, thereby the first trained model 122 can be generated. In this way, it becomes possible to realize the estimation of the energy device 310 at a higher accuracy in a variety of surgical situations. The same can be said for each of the other training data, training models, and trained models. The processing section 510 then transfers the trained model 121 thus generated to the controller 100, and the trained model 121 is stored in the storage section 120 of the controller 100.

Figure 13:
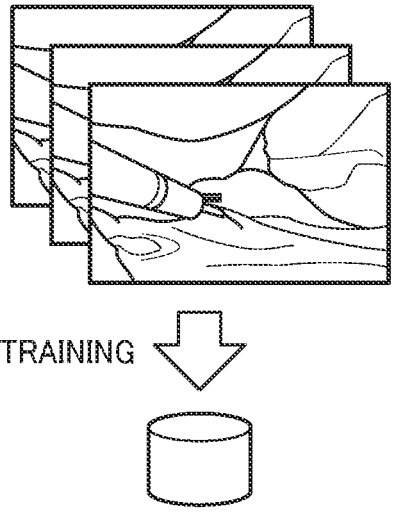
FIG. 13 is an explanatory view of a training phase for estimation of energy device.

FIGS. 13 to 17 explain the details of the aforementioned training phase. FIG. 13 is an explanatory view of the first trained model 122 used for the estimation of the energy device 310 in the device detection section 112. As shown in FIG. 13, in the training device 500, the first training data 521A labeled with annotations corresponding to the pre-treatment image of the energy device 310 and the biological tissue is fed back to the first training model 522A to modify the existing first trained model 122, and the new first trained model 122 is input to the controller 100. The content of the annotation is correct answer data, such as the type, the position, and the range of the presence of the energy device 310, or the configuration and the condition or the like of the distal end section of the energy device 310.

Figure 14:
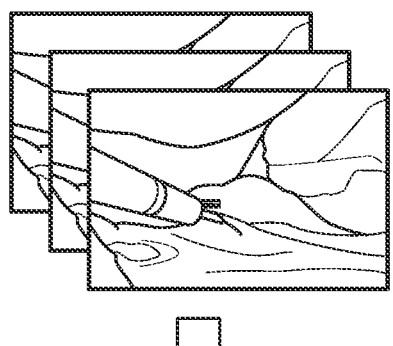
FIG. 14 is an explanatory view of a training phase for estimation of type of biological tissue.

FIG. 14 is an explanatory view of the second trained model 123 used for the estimation of biological tissue in the tissue detection section 111. Similarly to the case shown in FIG. 13, in the training device 500, the second training data 521B labeled with annotations corresponding to the pre-treatment image is fed back to the second training model 522B to modify the existing second trained model 123, and the new second trained model 123 is input to the controller 100. The content of the annotation is correct answer data, such as the name of the tissue present in the pre-treatment image, the range of the presence of each tissue, the condition of each tissue, and the like.

Figure 15:
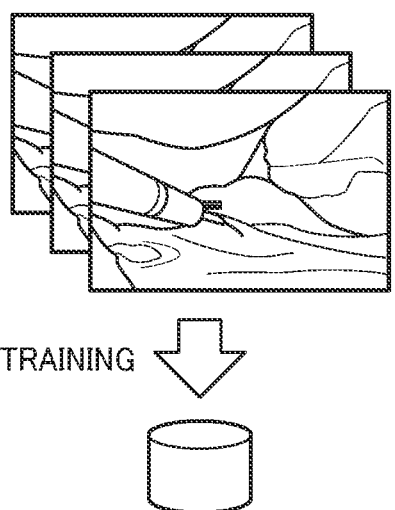
FIG. 15 is an explanatory view of a training phase for estimation of tension on a treatment target tissue.

FIG. 15 is an explanatory view of the fourth trained model 125 used for the estimation of the tension applied on the treatment target tissue in the tissue tension evaluation section 113. In the training device 500, the fourth training data 521D labeled with annotations corresponding to the pre-treatment image is fed back to the fourth training model 522D to modify the existing fourth trained model 125, and the new fourth trained model 125 is input to the controller 100. The content of the annotation is correct answer data, such as the name of the treatment target tissue or the range of the presence of the treatment target tissue, the amount of tension applied in the region, and the like.

The fourth training data 521D for the tension application amount can be acquired, for example, from the setting of the energy device 310.

Figure 16:
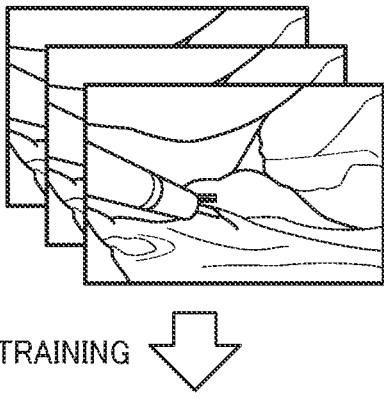
FIG. 16 is an explanatory view of a training phase for estimation of gripping force.

FIG. 16 is an explanatory view of the fifth trained model 126 used for the estimation of gripping force in the gripping force evaluation section 114. In the training device 500, the fifth training data 521E labeled with annotations corresponding to the pre-treatment image is fed back to the fifth training model 522E to modify the existing fifth trained model 126, and the new fifth trained model 126 is input to the controller 100. The contents of the annotations are correct answer data, including the tension application amount, the amount of change of tissue around the grip section, the gripping force, and the like. The fifth training data 521E for the tension application amount can be acquired, for example, from the setting of the energy device 310, similarly to the case of FIG. 15. The gripping force can also be acquired from the setting of the energy device 310. The amount of change of tissue around the grip section can be extracted, for example, from the history information of the pre-treatment image.

Figure 17:
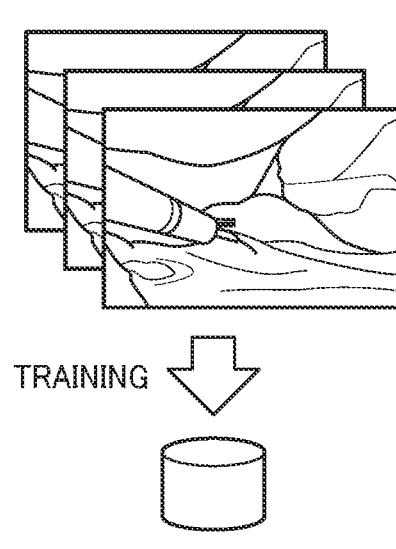
FIG. 17 is an explanatory view of a training phase for estimation of estimated heat diffusion region.

FIG. 17 is an explanatory view of the sixth trained model 127 used for the estimation of the heat diffusion region in the thermal invasion region prediction section 116. In the training device 500, the sixth training data 521F labeled with annotations corresponding to the pre-treatment image is fed back to the sixth training model 522F to modify the existing sixth trained model 127, and the new sixth trained model 127 is input to the controller 100. The contents of the annotations are correct answer data, including the tissue type, the tissue condition, the gripping amount, the application amount of tissue tension, the gripping force, the output setting, the type of the energy device 310, the output history, and heat diffusion region after the treatment, and the like. For example, the doctor may perform labeling of some of the correct answer data.

One of the keys to usual energy treatment in surgery is to suppress heat diffusion from the energy device to avoid thermal damages to surrounding organs. However, because the tissues to be treated are not uniform, the time required for the procedure, such as division, varies due to the difference in tissue type, the difference in tissue condition, individual differences of the patients, or the like; accordingly, the degree of heat diffusion also varies. To cope with these issues and suppress the heat diffusion, the doctors have been adjusting the amount of the tissue gripped by the energy device and the tissue tension; however, an appropriate adjustment may be difficult in some cases, in particular for non-experts with fewer experiences. Therefore, in order to proceed with the manipulation more efficiently, it is desirable to have support from the system.

As described above, in the treatments using energy devices, it is often necessary to watch the heat diffusion to the surrounding area, and the doctors perform the treatments while estimating the degree of heat diffusion. In the Japanese Unexamined Patent Application Publication No. 2021-83969 described above, an already-ablated biological tissue region and a not-yet-ablated biological tissue region are displayed on a display to indicate to the doctor the region of biological tissue to which energy should be output next. However, because the output is performed by estimating the temperature change from the difference between the CT image before the energy output and the CT image after the start of energy output, only the temperature change at or after the start of heat output can be estimated, and the appropriate position of the treatment tool cannot be presented before the start of heat output. In addition, the range of a critical tissue is unknown in some cases.

In this regard, according to the present system, the estimation of the heat diffusion region is performed based on the information of the energy device, the biological tissue, and the like, and the estimated heat diffusion region is superimposed on the display screen. This allows the doctor to grasp in advance the heat diffusion region and make the output setting of the energy device in a way such that thermal damages to the treatment target tissue can be avoided. In addition, the present system performs the estimation of the heat diffusion region by using machine learning, thus making it possible to perform safe and efficient surgery and improve stability in surgery regardless of the doctor's experience.

5. Second Embodiment

Figure 18:
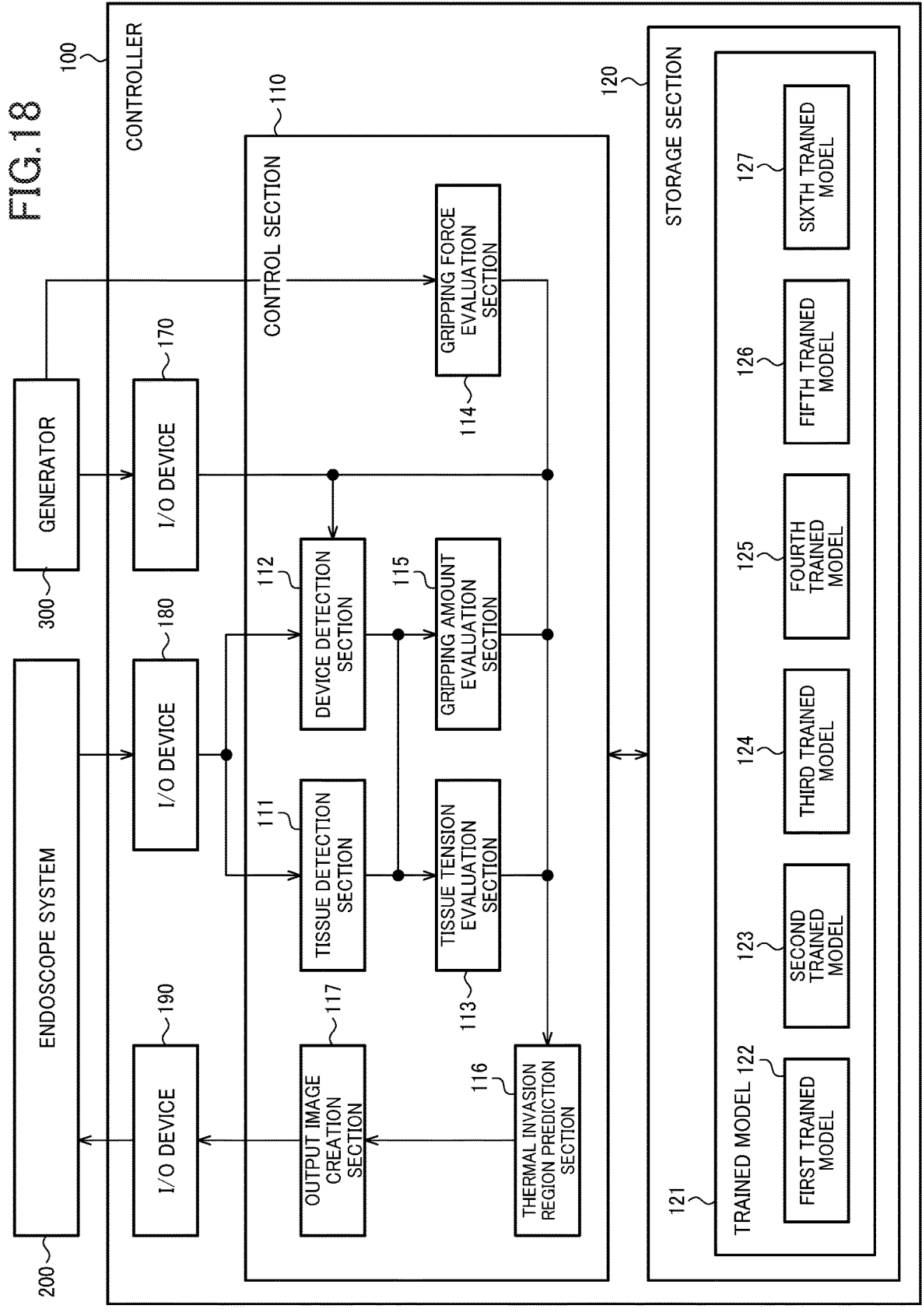
FIG. 18 is a configuration example of a controller according to a second embodiment.

FIG. 18 is a configuration example of the controller 100 according to the second embodiment of the present system. The gripping force evaluation section 114 of the second embodiment differs from that in the first embodiment shown in FIG. 2. Specifically, in the first embodiment, the information input to the gripping force evaluation section 114 is output from the tissue tension evaluation section 113 and the gripping amount evaluation section 115; however, in the second embodiment, the information input to the gripping force evaluation section 114 is output from the generator 300 provided outside the controller 100. That is, in the second embodiment, the gripping force evaluation section 114 detects the gripping force of the energy device 310 by acquiring information from the generator 300 provided outside the controller 100. The generator 300 is capable of acquiring a detection value of the gripping force from, for example, a gripping force detection sensor, such as a stress sensor, a position meter, or the like, mounted on the handle of energy device 310. Then, the control section 110 estimates the estimated heat diffusion region based on the pre-treatment image, the information regarding the energy supply amount, and the gripping force acquired from the gripping force detection sensor.

Figure 19:
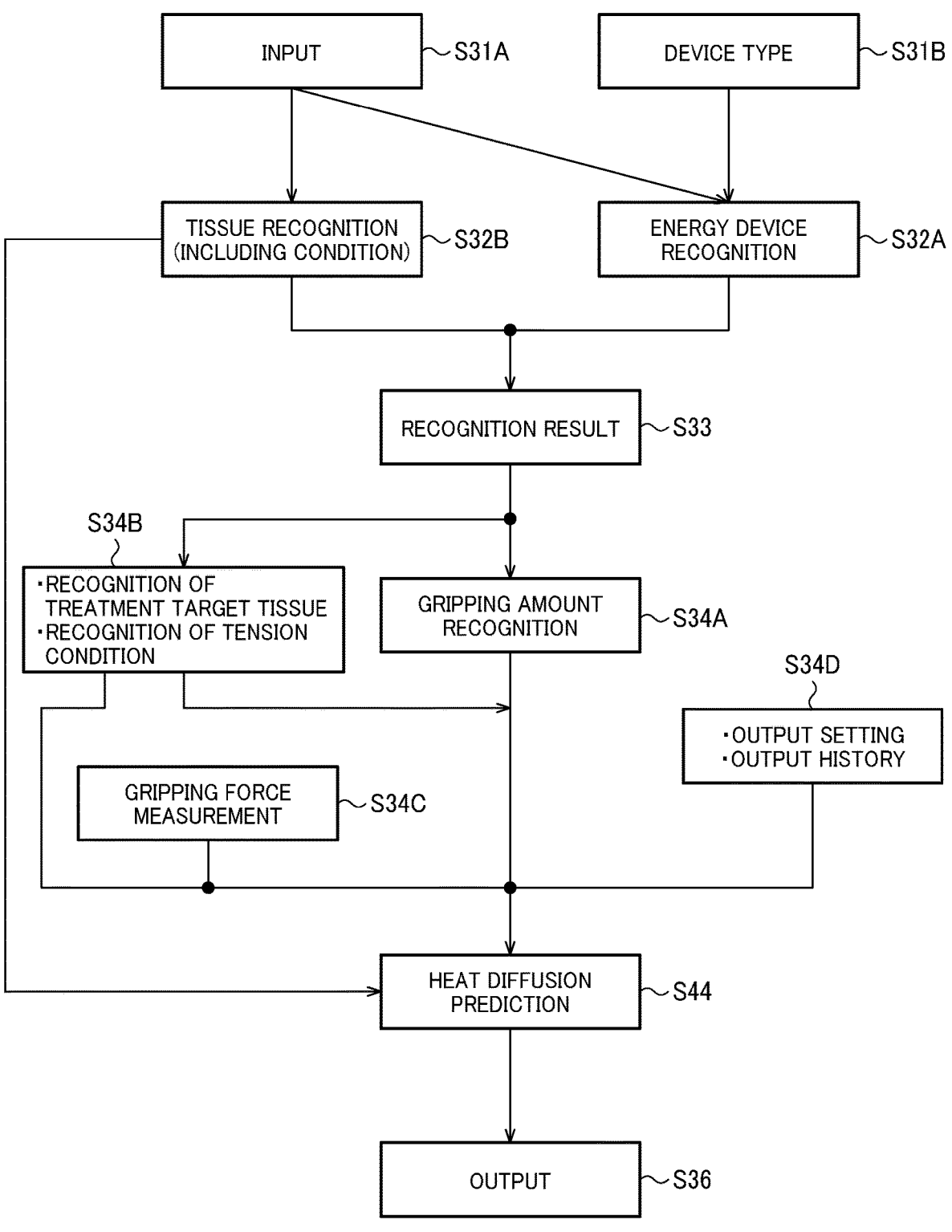
FIG. 19 is an example of processing according to the second embodiment.

FIG. 19 is an example of the processing according to the second embodiment of the present system. Compared to the aforementioned example of processing in the first embodiment in FIG. 8, in FIG. 19, the measurement of gripping force shown in S34C is performed instead of the estimation of gripping force in S25. Further, in the second embodiment, the gripping force evaluation section 114 does not acquire the output result of the tissue tension evaluation section 113, but acquires the detection value of the gripping amount from an external device, such as the generator 300.

According to the second embodiment, by using the data measured by the gripping force detection sensor of the energy device 310, the estimation process in the gripping force evaluation section 114 can be skipped. This enables acceleration of the process of estimation of the heat diffusion region. In addition, in some cases, the certainty factor of the base data may be low in the estimation process in the gripping force evaluation section 114. In this case, even if a certain period of time is taken for the estimation process, the certainty factor of the estimation result may also be low, and if the doctor performs a surgery using such uncertain estimation results, it will be difficult to perform an efficient surgery. Therefore, according to the second embodiment, efficient surgery can be performed while maintaining more safety.

6. Third Embodiment

Figure 20:
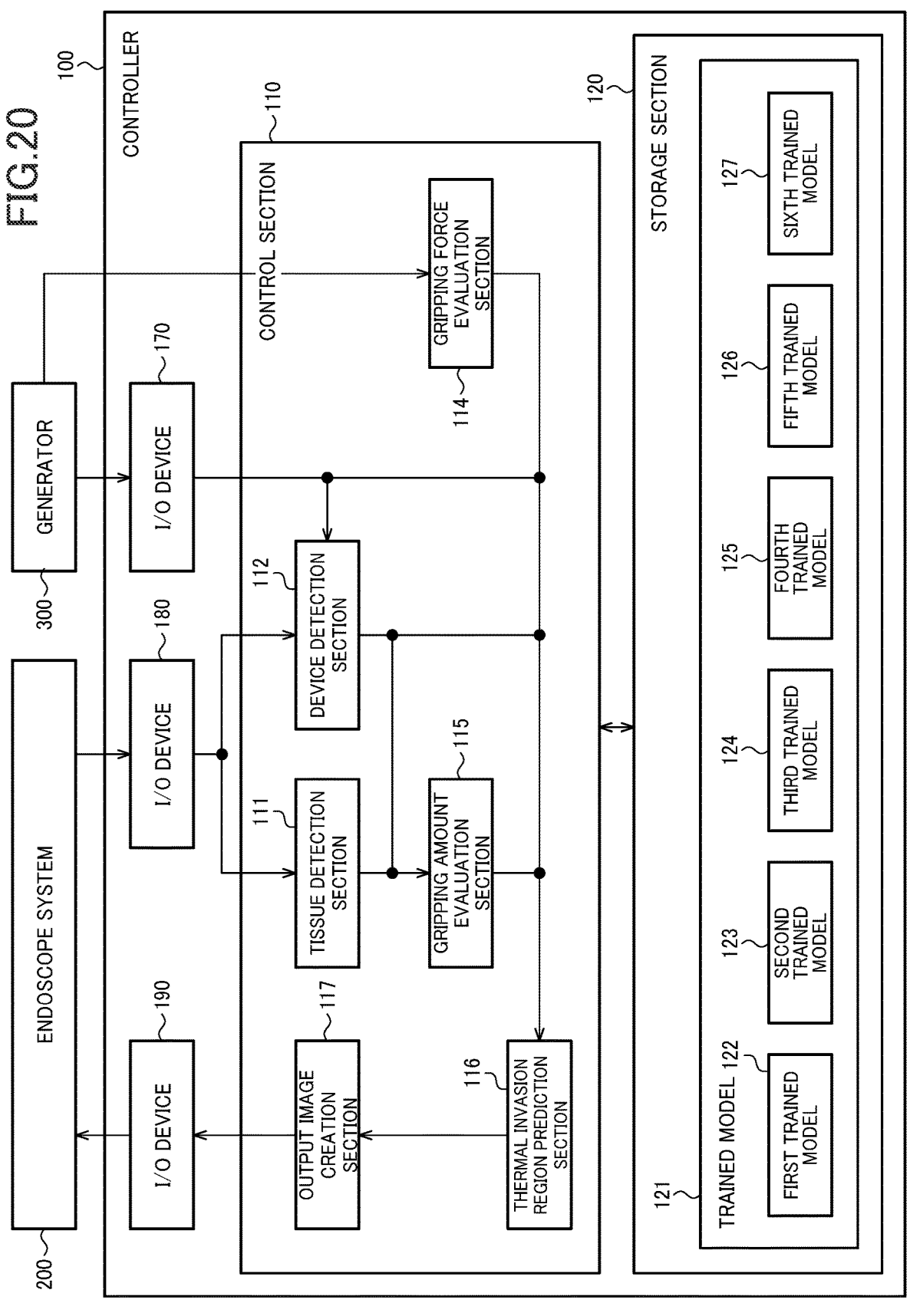
FIG. 20 is a configuration example of a controller according to a third embodiment.
Figure 21:
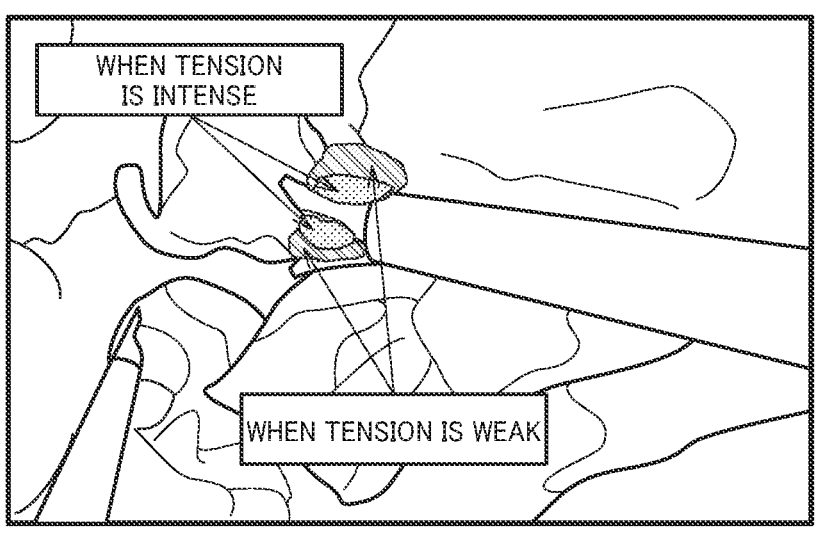
FIG. 21 is a display example of an estimated heat diffusion region in application of the third embodiment.

FIG. 20 is a configuration example of the controller 100 according to the third embodiment of the present system. The third embodiment differs from the second embodiment shown in FIG. 18 in that the tissue tension evaluation section 113 is not provided. That is, in the third embodiment, the tissue tension is not estimated by machine learning; instead, the estimation of the heat diffusion region is performed. Then, the heat diffusion region that varies depending on the application amount of tissue tension, i.e., the tension applied to the biological tissue, is superimposed on the display screen. For example, both the heat diffusion prediction range when the tension is intense and the heat diffusion prediction range when the tension is low are presented. Further, it is also possible to estimate an estimated heat diffusion region corresponding to each of a plurality of stages of tension intensity. In this case, the plurality of stages may be gradations. FIG. 21 shows application of the third embodiment, showing an example of an image in which the estimated heat diffusion region when the tension is intense and the estimated heat diffusion region when the tension is weak are respectively superimposed on the pre-treatment image to be displayed. When the tension applied on the tissue is intense, the estimated heat diffusion region is displayed in a narrow range on both sides of the jaw at the distal end section of the energy device 310. Then, when the tension applied on the tissue is weak, the estimated heat diffusion region is displayed in a wide range on both sides of the jaw.

Figure 22:
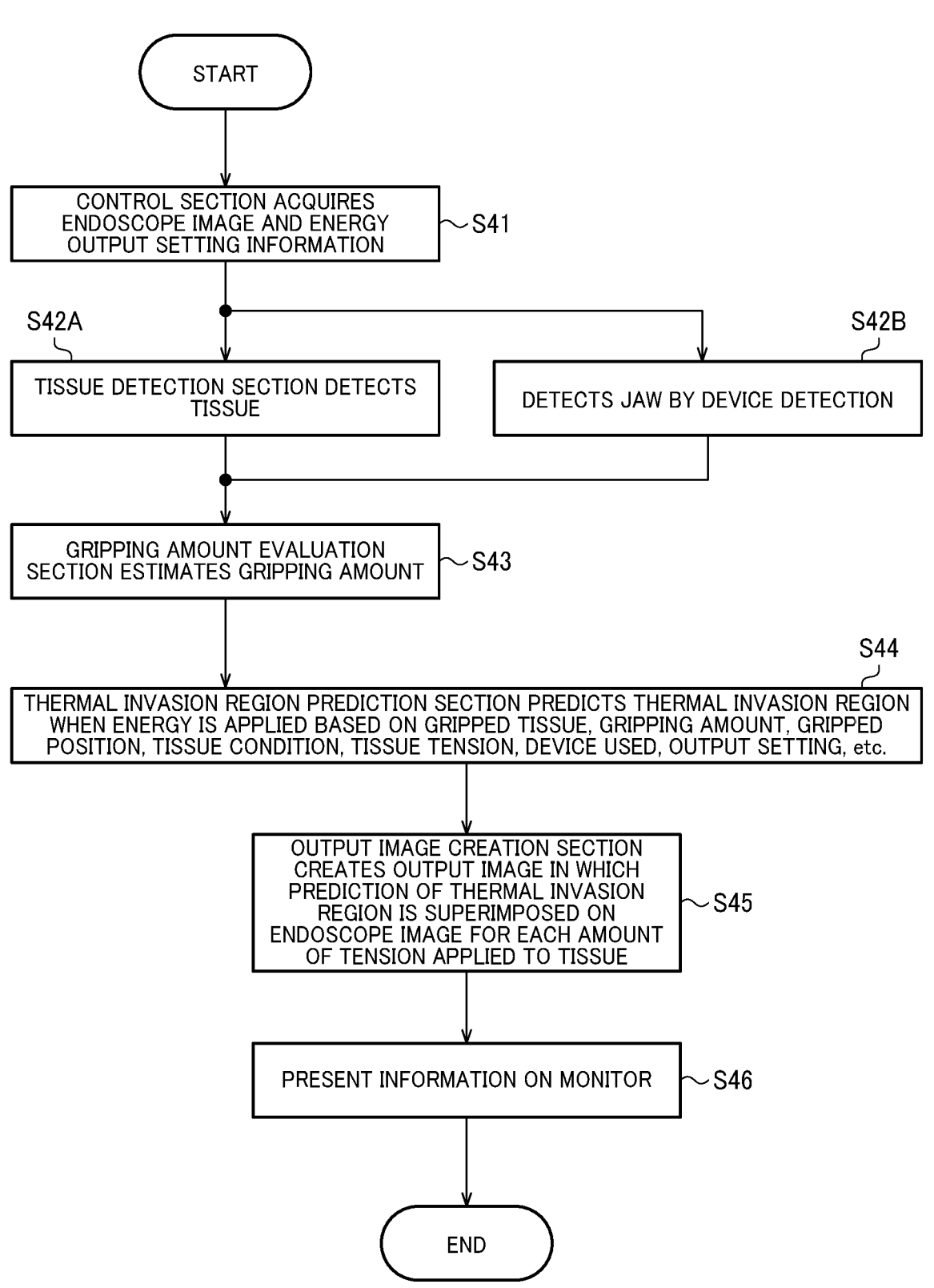
FIG. 22 is an example of processing according to the third embodiment.

FIG. 22 shows an example of the processing according to the third embodiment. Compared to the aforementioned example of the processing in the first embodiment in FIG. 3, the step of evaluating the tension applied to the tissue in the step S3A1 is omitted. There is also no step of estimating the gripping force in the gripping force evaluation section 114 shown in S3A2 of FIG. 3. Further, in the third embodiment shown in FIG. 22, in the step S45, the prediction of the thermal invasion region is displayed by being superimposed on the endoscope image for each amount of tension applied to the tissue.

In this way, in the third embodiment, the estimation process in the tissue tension evaluation section 113 and the gripping force evaluation section 114 can be skipped. Therefore, the process of estimating the heat diffusion region can be further accelerated compared to the case of the second embodiment.

Further, as a modification example of the third embodiment, the control section 110 may estimate the estimated heat diffusion region corresponding to each of the plural stages of the gripping amount without estimating the gripping amount of the energy device 310 imaged in the pre-treatment image. In this way, the estimation process in the gripping amount evaluation section 115 can be skipped, thus the process of estimating the estimated heat diffusion region can be accelerated.

7. Fourth Embodiment

As in the first and second embodiments, after measuring the tension applied to the tissue and the amount of tissue gripped by the energy device 310, if the certainty factors of the estimated tension and the gripping amount are lower than a predetermined value, the best case and the worst case for the tension and the gripping amount may be displayed. Further, in this case, it is also possible to estimate the estimated heat diffusion region corresponding to each of a plurality of stages for each parameter. That is, in the fourth embodiment, for example, if the certainty factor in the estimation of the tension applied to the tissue is lower than the first predetermined value, the estimated heat diffusion region corresponding to each of plural stages of tension is estimated without using the estimated tension. Then, if the certainty factor in the estimation of the gripping amount is lower than the second predetermined value, the heat diffusion region corresponding to each of plural stages of gripping force is estimated without using the estimated gripping force. The first predetermined value and the second predetermined value are reference values for determining that the certainty factor of the tension value estimated by machine learning is low and therefore is inappropriate in use for the estimation of the estimated heat diffusion region, and can be set arbitrarily by the doctor, for example. In the present embodiment, the doctor will be able to select appropriate energy setting from the displayed information of the estimated heat diffusion region for each stage, thereby can perform the surgery safely and efficiently. Further, in the fourth embodiment, if the certainty factors of other parameters than the tension or gripping amount are lower than the predetermined value, the estimated value of the parameter may not be used to estimate the estimated heat diffusion region. The fourth embodiment may be applied when the certainty factor of either or both of the tension and the gripping amount is low. The first predetermined value and the second predetermined value may be the same or different.

Further, in the present embodiment, the control section 110 may also estimate the estimated heat diffusion region for each temperature or heat, and superimpose the estimated heat diffusion region for each temperature or heat thus estimated on the pre-treatment image to display the estimated heat diffusion region. That is, the control section 110 may superimpose the estimated heat diffusion region around the recognized energy device 310 and the biological tissue by changing the color for each variable, temperature, and heat to display the estimated heat diffusion region.

Figure 23:
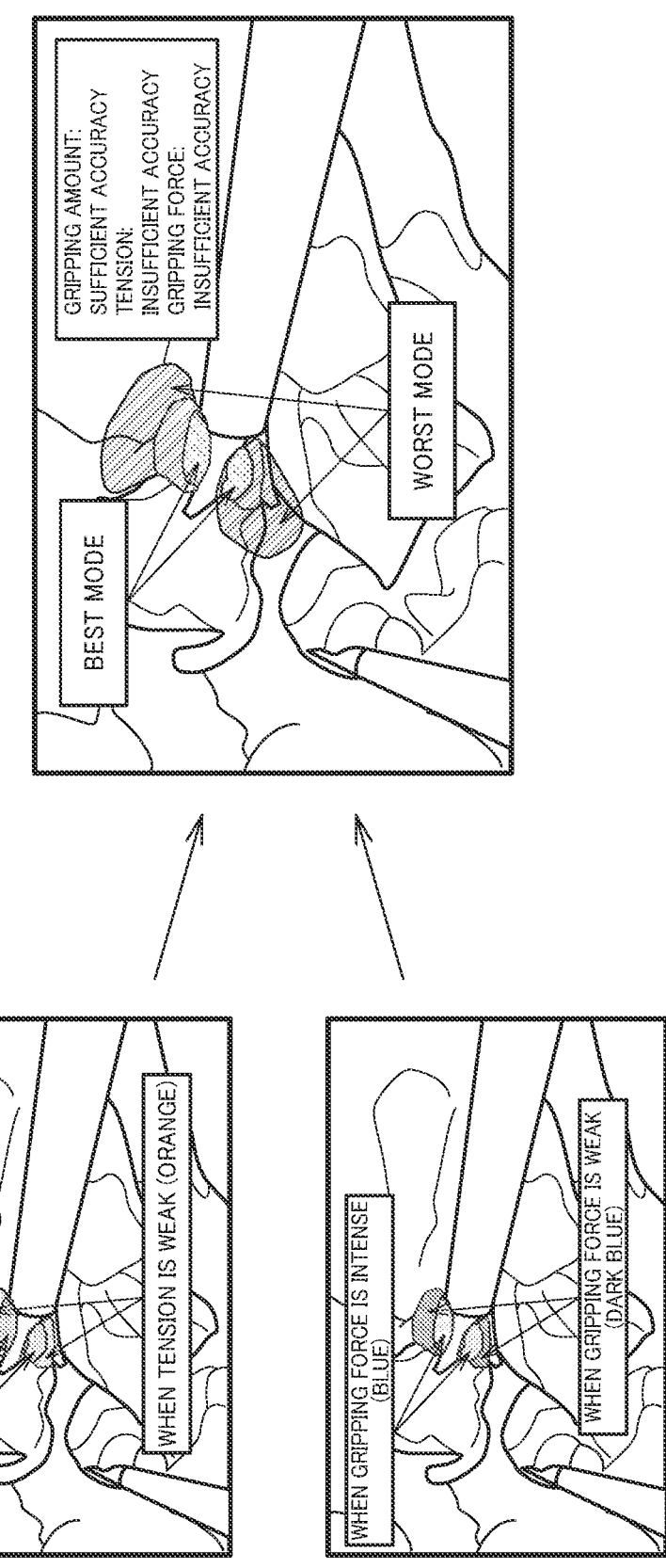
FIG. 23 is a display example of an estimated heat diffusion region showing a best mode and a worst mode.

Regarding the color, for example, a color tone between the color for displaying the tension and the color for displaying the gripping force may be used for the display. For example, as shown on the left side of FIG. 23, the tension has a warm color, for example, red is shown when the tension is intense and orange is shown when the tension is weak, and the gripping force has a cold color, for example, blue is shown when the gripping force is intense and dark blue is shown when the gripping force is weak. In this case, as shown on the right side of the same figure, upon the display of the estimated heat diffusion region, they are integrated and displayed with intermediate colors. Then, for the parameters of the tension and the gripping force, display indicating that the accuracy is insufficient may be performed. Further, for example, it is possible to display information indicating that the best mode is a case where the tension and the gripping amount are intense, which makes the estimated heat diffusion region narrowest, and that the worst mode is a case where the tension and the gripping force are weak, which makes the estimated heat diffusion region largest. In this way, the doctor will be able to grasp which parameters have a low certainty factor and will be able to determine, based on the color, what combination of the plural parameters with low certainty factors can be used to set the best mode. It is not easy for a doctor to determine what type of combination of parameter setting would minimize the heat diffusion region when there are a plurality of parameters having a low certainty factor. Therefore, in this way, it is possible to support the doctor's decision by presenting a combination that minimizes the heat diffusion region from among the possible combinations of the parameters by using machine learning.

Figures 24, 25:
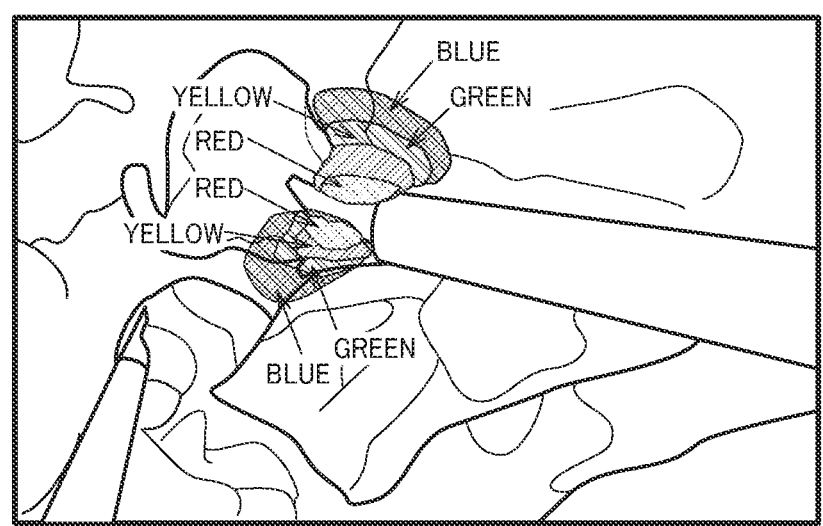
FIG. 24 is a table showing the relationship between a combination of tension and gripping force and a corresponding color.
FIG. 25 is a display example of an estimated heat diffusion region in application of a fourth embodiment.

Further, FIGS. 24 and 25 are examples in which, when there are a plurality of parameters having a low certainty factor, a color is set for each of all possible combinations of the setting values of the parameters, and is displayed on the screen. FIG. 24 shows all possible combinations of the tension and the gripping force with intense or weak setting values, and the colors corresponding to these combinations. FIG. 25 is an example of an image showing how the estimated heat diffusion regions are distributed by showing the corresponding colors, when the parameter combinations shown in FIG. 24 are used. In the case shown in FIG. 25, it can be seen that the estimated heat diffusion region becomes narrowest when both the tension and the gripping force are intense.

8. Fifth Embodiment

Figure 26:
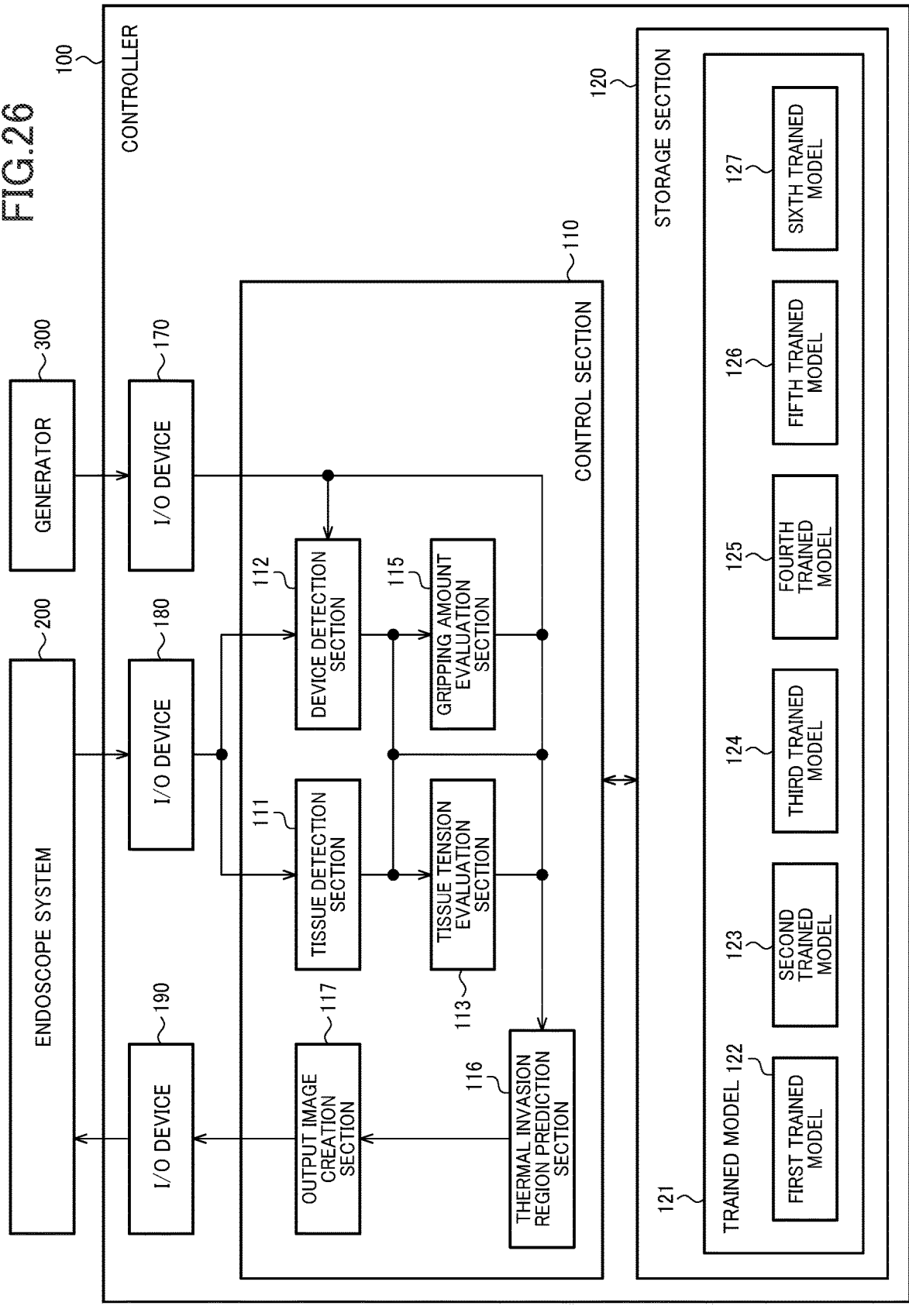
FIG. 26 is a configuration example of a controller according to a fifth embodiment.
Figure 27:
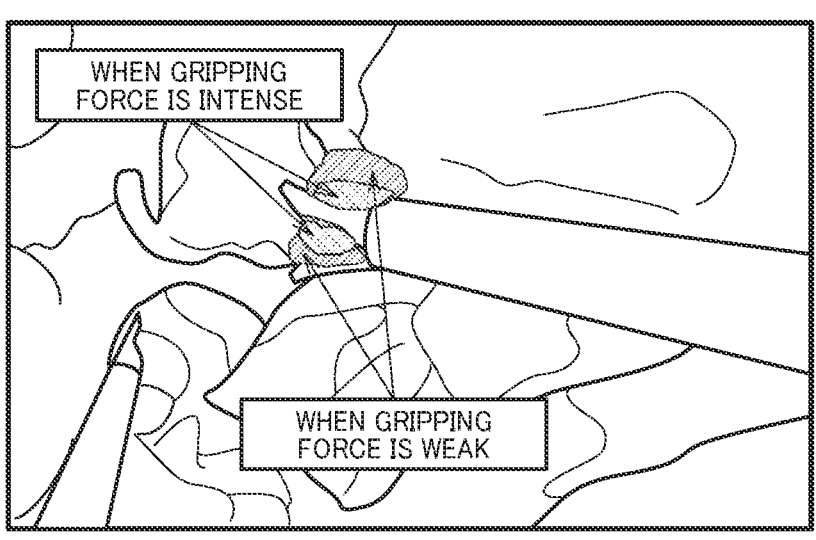
FIG. 27 is a display example of an estimated heat diffusion region in application of the fifth embodiment.

FIG. 26 is a configuration example of the controller 100 according to the fifth embodiment of the present system. The fifth embodiment differs from the first embodiment shown in FIG. 2 in that the gripping force evaluation section 114 is omitted. That is, in the fifth embodiment, the estimation of the heat diffusion region is performed without estimating the gripping force by machine learning. Then, the heat diffusion region that varies depending on the gripping force is superimposed on the display screen. At this time, the information of gripping force is input to the fifth training data 521E, and the estimated heat diffusion regions for various degrees of gripping force are estimated and superimposed on the pre-treatment image and are displayed. FIG. 27 shows application of the fifth embodiment, showing an example of an image in which the estimated heat diffusion region when the gripping force is intense and the estimated heat diffusion region when the gripping force is weak are respectively superimposed on the pre-treatment image and are displayed. In the case shown in FIG. 27, when the gripping force of the energy device 310 is intense, the estimated heat diffusion region is displayed in a narrow range on both sides of the jaw at the distal end section of the energy device 310. Then, when the gripping force is weak, the estimated heat diffusion region is displayed in a wide range on both sides of the jaw. Further, in this case, it is also possible to estimate the estimated heat diffusion region corresponding to each of a plurality of stages of the degree of gripping force.

Figure 28:
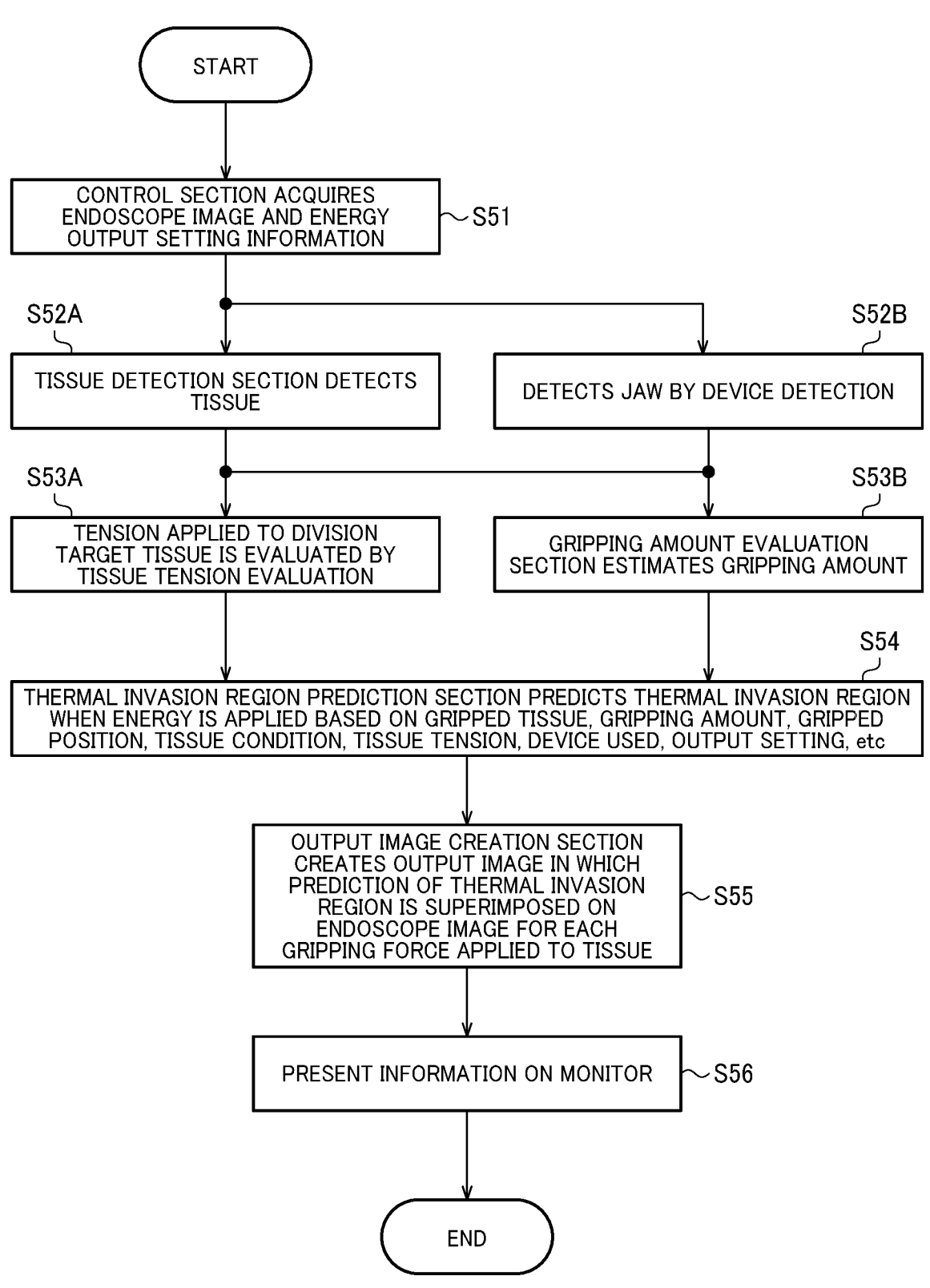
FIG. 28 is a flowchart for explaining processing performed by a controller and a system in application of the fifth embodiment.

FIG. 28 is a flowchart for explaining processing performed by the controller 100 and the system 10 in application of the fifth embodiment. Compared to the flowchart shown in FIG. 3, the step of estimating the gripping force in the gripping force evaluation section 114 in the step S3A2 of FIG. 3 is omitted. Further, in the step S5 of FIG. 3, in the fifth embodiment, the prediction of the thermal invasion region is superimposed on the endoscope image for each gripping force applied to the tissue to create the output image.

According to the fifth embodiment, the heat diffusion region that varies depending on the gripping force can be superimposed on the display screen to be displayed without measuring the gripping force. Therefore, it is not necessary to provide a sensor or the like for detecting the gripping force or the like in the energy device 310 or the like, thereby the present system can be realized at a low cost. Further, sterilization of the energy device 310 may also be simplified.

Figure 29:
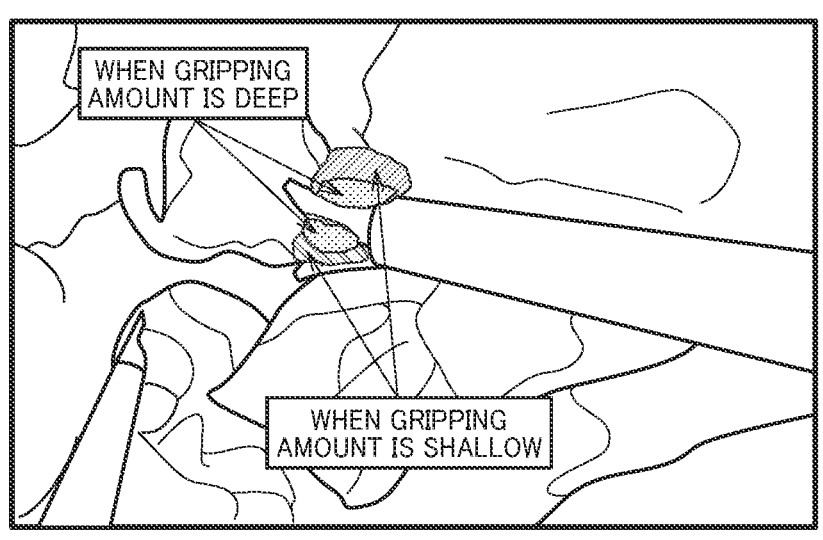
FIG. 29 is a display example of an estimated heat diffusion region when estimation of gripping amount is not performed.

Although the fifth embodiment is a case where the estimated heat diffusion region is estimated without estimating the gripping force, the same can be applied to other parameters, for example, the gripping amount of the biological tissue. FIG. 29 is an example of an image in which the estimated heat diffusion regions are superimposed in different patterns respectively for a case with a deep gripping amount and a case with a shallow gripping amount, without performing the estimation of the gripping amount.

9. Sixth Embodiment

Figure 30:
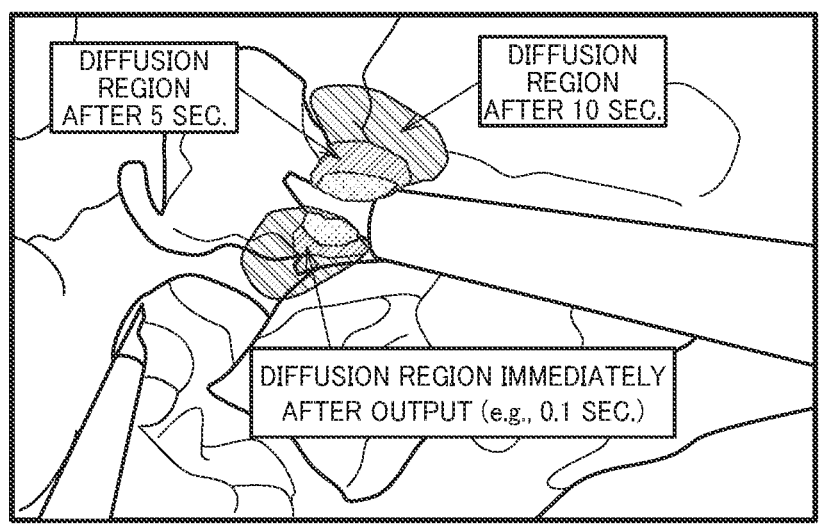
FIG. 30 is a display example of an estimated heat diffusion region in application of a sixth embodiment.

FIG. 30 is a display example of estimated heat diffusion region in application of the sixth embodiment of the present system. As shown in FIG. 30, the estimated heat diffusion regions at 0.1 second, 5 seconds, and 10 seconds after the start of energy application are respectively superimposed on the endoscope image and are displayed. For example, even if the estimated heat diffusion region immediately after the output is narrow, the estimated heat diffusion region may soon become wider thereafter depending on the heat conduction and the tissue condition of the treatment target tissue and surrounding tissue thereof. Therefore, according to the sixth embodiment, the doctor can grasp the extent to which the estimated heat diffusion region extends as a result of continuous application of energy, thereby can perform the surgery more safely and efficiently.

Further, the system of the present embodiment can also be realized as a program. Specifically, a pre-treatment image, in which at least one energy device and at least one biological tissue are imaged, in which a state before application of energy from the energy device is imaged, and that is captured by a camera that captures an image of a surgical field, is acquired, and information regarding the energy supply amount to be supplied to the energy device is acquired. Further, an estimated heat diffusion region, which is an estimated range of reach of the energy after the application of energy from the energy device based on the energy supply amount in the pre-treatment image is estimated by processing based on a trained model that has been trained to output, from the training device tissue image, in which at least one energy device and at least one biological tissue are imaged, or from the training tissue image, in which the at least one biological tissue is imaged, a heat diffusion region that is a range of reach of heat from the energy device. Then, a computer is caused to perform a process of causing a display section to superimpose the estimated heat diffusion region on a captured image of the camera to display the estimated heat diffusion region. The computer assumed herein may be a network terminal or the like, such as a personal computer or the like. However, the computer may also be a wearable terminal such as a smartphone, a tablet, a smartwatch, or the like. In this way, the same effects as those described above can be achieved.

Further, the system of the present embodiment can also be realized as an information processing method. Specifically, in the information processing method, a pre-treatment image, in which at least one energy device and at least one biological tissue are imaged, in which a state before application of energy from the energy device is imaged, and that is captured by a camera that captures an image of a surgical field, is acquired, and information regarding the energy supply amount to be supplied to the energy device is acquired. Further, an estimated heat diffusion region, which is an estimated range of reach of the energy after the application of energy from the energy device based on the energy supply amount in the pre-treatment image is estimated by processing based on a trained model that has been trained to output, from the training device tissue image, in which at least one energy device and at least one biological tissue are imaged, or from the training tissue image, in which the at least one biological tissue is imaged, a heat diffusion region that is a range of reach of heat from the energy device. Then, the estimated heat diffusion region is superimposed on a captured image of the camera, and is displayed on the display section. In this way, the same effects as those described above can be achieved.

The system 10 of the present embodiment described above includes the storage section 120 that stores the trained model 121 and the control section 110. The trained model 121 is trained to output a heat diffusion region from the training device tissue image or the training tissue image. The training device tissue image is an image in which at least one energy device, which receives energy supply and performs energy output, and at least one biological tissue are imaged. The training tissue image is an image in which at least one biological tissue is imaged. The control section 110 acquires a pre-treatment image, in which at least one energy device and at least one biological tissue are imaged, in which a state before application of energy from the energy device 310 is imaged, and that is captured by a camera that captures an image of a surgical field. The control section 110 acquires information regarding the energy supply amount supplied to the energy device. The control section 110 estimates, based on the pre-treatment image, the information regarding the energy supply amount, and the trained model, an estimated heat diffusion region, which is an estimated range of reach of energy from the energy device after application of the energy based on the energy supply amount, in the pre-treatment image. Then, the control section 110 causes a display section to superimpose the estimated heat diffusion region on a captured image of the camera to display the estimated heat diffusion region.

As a result, in some embodiments, the heat diffusion region is estimated based on the pre-treatment image and the information regarding the energy supply amount, and the estimated heat diffusion region is superimposed on the display screen and is displayed. This allows the doctor to grasp in advance the heat diffusion region and make the output setting of the energy device 310 in a way such that thermal damages to the treatment target tissue can be avoided. In addition, by performing the estimation of the heat diffusion region using machine learning, it is possible to perform safe and efficient surgery and improve stability in surgery regardless of the doctor's experience. The tissue information is described, for example, in the section "1. System".

Further, in the present embodiment, the control section 110 may also extract the tissue information, which is information regarding the biological tissue imaged in the pre-treatment image, from the pre-treatment image, and estimate the estimated heat diffusion region based on the tissue information and the information regarding the energy supply amount.

As a result, in some embodiments, the treatment target tissue can be extracted by machine learning using pre-treatment images. Therefore, the estimated heat diffusion region can be estimated based on this.

Further, in the present embodiment, the control section 110 may also extract, from the pre-treatment image, device information, which is information regarding the energy device 310 imaged in the pre-treatment image, and may estimate the estimated heat diffusion region in the treatment target tissue to be treated by the energy device 310 based on the device information and the tissue information.

As a result, in some embodiments, the treatment target tissue and the energy device 310 can be extracted by machine learning using pre-treatment images. Therefore, the estimation of estimated heat diffusion region can be performed based on these items of information. The device information is described in the section "4. First Embodiment".

Further, in the present embodiment, the control section 110 estimates regions of the treatment target tissue and the energy device 310 in the pre-treatment image, based on the tissue information and the device information. The control section 110 estimates, based on the estimated regions of the treatment target tissue and the energy device 310, at least one of the tension applied to the biological tissue imaged in the pre-treatment image and the gripping amount of the energy device as an estimation result. The control section 110 estimates the estimated heat diffusion region based on the estimation result, the tissue information, and the information regarding the energy supply amount.

As a result, in some embodiments, the estimated heat diffusion region can be estimated by machine learning using the estimation results for the tension applied to the biological tissue and the gripping amount of the energy device. The tension applied to the biological tissue is described in the section "2. Controller" and the gripping amount of the energy device is described in the section "4. First Embodiment".

Further, in the present embodiment, the control section 110 may estimate the gripping force of the energy device 310 based on the estimated tension and the pre-treatment image, and may estimate the estimated heat diffusion region based on the estimated gripping force.

As a result, in some embodiments, the gripping force of the energy device 310 can be estimated by machine learning based on the tension estimated by the control section 110 and the pre-treatment image. Therefore, it is possible to estimate the estimated heat diffusion region using the gripping force.

Further, in the present embodiment, the control section 110 may also acquire a detection value of the gripping force detected by a gripping force detection sensor provided in the grip section of the energy device 310, and may estimate the estimated heat diffusion region based on the acquired detection value.

As a result, in some embodiments, by using the data measured by the gripping force detection sensor, the estimation process in the gripping force evaluation section 114 can be skipped. This enables acceleration of the process of estimation of the estimated heat diffusion region. In addition, when the certainty factor of the data of the gripping force, which is used as the base of the estimation, is low, the data measured by the gripping force detection sensor can be used to achieve safe and efficient surgery.

Further, in the present embodiment, the control section 110 may also estimate the estimated heat diffusion region for each temperature or heat, and superimpose the estimated heat diffusion region for each temperature or heat thus estimated on the pre-treatment image to display the estimated heat diffusion region.

As a result, in some embodiments, the control section 110 is capable of superimposing the estimated heat diffusion region around the recognized energy device 310 and the biological tissue by changing the color for each variable, temperature, and heat, to display the estimated heat diffusion region.

Further, in the present embodiment, the control section 110 may also estimate the region of the biological tissue and the region of the energy device 310 from the pre-treatment image, and superimpose the estimated heat diffusion region on the estimated region of biological tissue around the energy device 310 to display the estimated heat diffusion region.

As a result, in some embodiments, the region of the biological tissue and the region of the energy device 310 can be estimated from the pre-treatment image by machine learning. Therefore, it is possible to display the estimated heat diffusion region by superimposing it on the pre-treatment image.

Further, in the present embodiment, the control section 110 may estimate the estimated heat diffusion region corresponding to each of plural stages of the tension without estimating the tension applied to the biological tissue imaged in the pre-treatment image.

As a result, in some embodiments, the estimation process in the tissue tension evaluation section 113 can be skipped. Therefore, the process of estimating the estimated heat diffusion region can be accelerated. The method of displaying the estimated heat diffusion region corresponding to each of the plural stages of the tension is described in FIG. 21 in the section "6. Third Embodiment".

Further, in the present embodiment, the control section 110 may estimate the estimated heat diffusion region corresponding to each of the plural stages of the gripping amount without estimating the gripping amount of the energy device 310 imaged in the pre-treatment image.

As a result, in some embodiments, the estimation process in the gripping amount evaluation section 115 can be skipped, thus the process of estimating the estimated heat diffusion region can be accelerated. The method of displaying the estimated heat diffusion region corresponding to each of the plural stages of the gripping amount is described in FIG. 29 in the section "8. Fifth Embodiment".

Further, in the present embodiment, the control section 110 estimates, based on the pre-treatment image, the tension applied to the biological tissue imaged in pre-treatment image and the gripping amount of the energy device 310. If the certainty factor in the estimation of the tension is lower than the first predetermined value, the control section 110 estimates the estimated heat diffusion region corresponding to each of the plural stages of the tension without using the estimated tension for the estimation of the estimated heat diffusion region. If the certainty factor in the estimation of the gripping amount is lower than the second predetermined value, the control section 110 estimates the estimated heat diffusion region corresponding to each of the plural stages of gripping amount without using the estimated gripping force for the estimation of the estimated heat diffusion region.

As a result, in some embodiments, it is possible to determine whether or not to use estimation values of the tension and the gripping amount for the estimation of the heat diffusion region depending on the certainty factors of these estimation values. In this way, when the certainty factor of the estimation value is low, it is possible to estimate the heat diffusion region corresponding to each of the plural stages of the tension and the gripping amount without using the estimation value. Therefore, the doctor will be able to select appropriate energy setting from the displayed information, thereby performing the surgery safely and efficiently. The first predetermined value and the second predetermined value are described in the section "7. Fourth Embodiment". The method of displaying the estimated heat diffusion region corresponding to each of the plural stages of the tension and the gripping amount is described in FIG. 23 in the section "7. Fourth Embodiment".

Further, in the present embodiment, the control section 110 may estimate the estimated heat diffusion region corresponding to each of the plural stages of the force of gripping the biological tissue by the energy device 310.

As a result, in some embodiments, the heat diffusion region that varies depending on the gripping force can be displayed while being superimposed on the display screen without measuring the gripping force. Therefore, it is not necessary to provide a sensor or the like for detecting the gripping force or the like in the energy device 310 or the like, thereby the present system can be realized at a low cost. An example of the display of the estimated heat diffusion region using the present embodiment is shown in FIG. 27.

Further, in the present embodiment, the control section 110 may estimate the estimated heat diffusion region corresponding to each of the plural stages of time for the energy device 310 to apply energy.

As a result, in some embodiments, the doctor can grasp the extent to which the estimated heat diffusion region extends as a result of continuous application of energy, thereby can perform the surgery more safely and efficiently. The method of displaying the estimated heat diffusion region corresponding to each of the plural stages of time is described in FIG. 30 in the section "9. Sixth Embodiment".

Further, the above processing may also be written as a program. That is, the program of the present embodiment causes the controller 100 to execute acquiring a pre-treatment image, acquiring information regarding an energy supply amount, estimating an estimated heat diffusion region that is an estimated range of reach of energy by processing based on the trained model 121, and superimposing the estimated heat diffusion region on a captured image of a camera to display the estimated heat diffusion region in a display section.

Further, the above processing may also be written as an information processing method. That is, the information processing method of the present embodiment acquires a pre-treatment image, acquires information regarding an energy supply amount, estimates an estimated heat diffusion region that is an estimated range of reach of energy by processing based on the trained model 121, and superimposes the estimated heat diffusion region on a captured image of a camera, to display the estimated heat diffusion region in a display section.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

The invention claimed is:

1. A system comprising:
a memory configured to store a trained model that is trained to output a heat diffusion region from a training device tissue image or a training tissue image, the heat diffusion region being a range of reach of heat from the at least one energy device, the training device tissue image being an image in which at least one energy device that receives energy supply to output energy and at least one biological tissue are imaged, the training tissue image being an image in which the at least one biological tissue is imaged; and
a processor, wherein the processor is configured to:
acquire a pre-treatment image, in which the at least one energy device and the at least one biological tissue are imaged, in which a state before application of energy from the at least one energy device is imaged, and that is captured by a camera that captures an image of a surgical field;
acquire information regarding an energy supply amount to the at least one energy device;
estimate, based on the pre-treatment image, the information regarding the energy supply amount, and the trained model, an estimated heat diffusion region in the pre-treatment image, the estimated heat diffusion region being an estimated range of reach of energy from the at least one energy device after application of the energy based on the energy supply amount; and
perform a process of superimposing the estimated heat diffusion region on a captured image of the camera and displaying the captured image with the superimposed estimated heat diffusion region on a display;
wherein the processor further:
extracts, from the pre-treatment image, tissue information regarding a biological tissue that is imaged in the pre-treatment image, estimates the estimated heat diffusion region based on the tissue information and the information regarding the energy supply amount;

extracts, from the pre-treatment image, device information regarding the at least one energy device that is imaged in the pre-treatment image, estimates, based on the device information and the tissue information, the estimated heat diffusion region in a treatment target tissue to be treated by the at least one energy device, estimates regions of the treatment target tissue and the at least one energy device in the pre-treatment image based on the tissue information and the device information, estimates, based on the estimated regions of the treatment target tissue and the at least one energy device, at least one of a tension applied to a biological tissue imaged in the pre-treatment image and a gripping amount of the at least one energy device as an estimation result, and estimates the estimated heat diffusion region based on the estimation result, the tissue information, and the information regarding the energy supply amount.

2. The system as defined in claim 1, wherein the processor estimates a gripping force of the at least one energy device based on the estimated tension and the pre-treatment image, and estimates the estimated heat diffusion region based on the estimated gripping force.

3. The system as defined in claim 1, wherein the processor acquires a detection value of a gripping force detected by a gripping force detection sensor provided in a grip section of the at least one energy device, and estimates the estimated heat diffusion region based on the acquired detection value.

4. The system as defined in claim 1, wherein the processor estimates the estimated heat diffusion region for each temperature or heat, superimposes the estimated heat diffusion region for the temperature or the heat that has been estimated on the pre-treatment image to display the estimated heat diffusion region.

5. The system as defined in claim 2, wherein the processor estimates a region of a biological tissue and a region of an energy device from the pre-treatment image, and superimposes the estimated heat diffusion region on a region of a biological tissue around the at least one energy device that has been estimated to display the estimated heat diffusion region.

6. The system as defined in claim 1, wherein the processor estimates the estimated heat diffusion region corresponding to each of plural stages of tension without estimating the tension applied to a biological tissue imaged in the pre-treatment image.

7. The system as defined in claim 1, wherein the processor estimates the estimated heat diffusion region corresponding to each of plural stages of gripping amount without estimating the gripping amount of the at least one energy device imaged in the pre-treatment image.

8. The system as defined in claim 1, wherein the processor estimates, based on the pre-treatment image, tension applied to a biological tissue imaged in the pre-treatment image and a gripping amount of the at least one energy device, when a certainty factor in the estimation of the tension is lower than a first predetermined value, the processor estimates the estimated heat diffusion region corresponding to each of plural stages of the tension without using the estimated tension for the estimation of the estimated heat diffusion region, and when a certainty factor in the estimation of the gripping amount is lower than a second predetermined value, the processor estimates the estimated heat diffusion region corresponding to each of plural stages of the gripping amount without using the estimated gripping amount for the estimation of the estimated heat diffusion region.

9. The system as defined in claim 1, wherein the processor estimates the estimated heat diffusion region corresponding to each of plural stages of gripping force for gripping a biological tissue by the at least one energy device.

10. The system as defined in claim 1, wherein the processor estimates the estimated heat diffusion region corresponding to each of plural stages of time for the at least one energy device to apply energy.

11. A computer-readable non-transitory information storage medium storing a program for causing a computer to at least execute:

acquiring a pre-treatment image, in which at least one energy device and at least one biological tissue are imaged, in which a state before application of energy from the at least one energy device is imaged, and that is captured by a camera that captures an image of a surgical field, and acquiring information regarding an energy supply amount to the at least one energy device, estimating an estimated heat diffusion region in the pre-treatment image by processing based on a trained model, the estimated heat diffusion region being an estimated range of reach of energy from the at least one energy device after application of the energy based on the energy supply amount, the trained model being trained to output a heat diffusion region from a training device tissue image or a training tissue image, the heat diffusion region being a range of reach of heat from the at least one energy device, the training device tissue image being an image in which the at least one energy device and the at least one biological tissue are imaged, the training tissue image being an image in which the at least one biological tissue is imaged, and superimposing the estimated heat diffusion region on a captured image of the camera and displaying the captured image with the superimposed estimated heat diffusion region on a display;

extracting, from the pre-treatment image, tissue information regarding a biological tissue that is imaged in the pre-treatment image, extracting, from the pre-treatment image, device information regarding the at least one energy device that is imaged in the pre-treatment image, estimating, based on the device information and the tissue information, the estimated heat diffusion region in a treatment target tissue to be treated by the at least one energy device, estimating regions of the treatment target tissue and the at least one energy device in the pre-treatment image based on the tissue information and the device information, estimating, based on the estimated regions of the treatment target tissue and the at least one energy device, at least one of a tension applied to a biological tissue imaged in the pre-treatment image and a gripping amount of the at least one energy device as an estimation result, and estimating the estimated heat diffusion region based on the estimation result, the tissue information, and the information regarding the energy supply amount.

12. An information processing method, comprising:

acquiring a pre-treatment image, in which at least one energy device and at least one biological tissue are imaged, in which a state before application of energy from the at least one energy device is imaged, and that is captured by a camera that captures an image of a surgical field, and acquiring information regarding an energy supply amount to the at least one energy device, estimating an estimated heat diffusion region in the pre-treatment image by processing based on a trained model, the estimated heat diffusion region being an estimated range of reach of energy from the at least one energy device after application of the energy based on the energy supply amount, the trained model being trained to output a heat diffusion region from a training device tissue image or a training tissue image, the heat diffusion region being a range of reach of heat from the at least one energy device, the training device tissue image being an image in which the at least one energy device and the at least one biological tissue are imaged, the training tissue image being an image in which the at least one biological tissue is imaged, superimposing the estimated heat diffusion region on a captured image of the camera and displaying the captured image with the superimposed estimated heat diffusion region on a display, extracting, from the pre-treatment image, tissue information regarding a biological tissue that is imaged in the pre-treatment image, extracting, from the pre-treatment image, device information regarding the at least one energy device that is imaged in the pre-treatment image, estimating, based on the device information and the tissue information, the estimated heat diffusion region in a treatment target tissue to be treated by the at least one energy device, estimating regions of the treatment target tissue and the at least one energy device in the pre-treatment image based on the tissue information and the device information, estimating, based on the estimated regions of the treatment target tissue and the at least one energy device, at least one of a tension applied to a biological tissue imaged in the pre-treatment image and a gripping amount of the at least one energy device as an estimation result, and estimating the estimated heat diffusion region based on the estimation result, the tissue information, and the information regarding the energy supply amount.

* * * * *